(12) United States Patent
Tsuno

(10) Patent No.: US 10,660,821 B2
(45) Date of Patent: May 26, 2020

(54) TEMPERATURE-REGULATED TRANSPORT BOX

(71) Applicant: FUJIFILM Toyama Chemical Co., Ltd., Chuo-ku (JP)

(72) Inventor: Katsuhiro Tsuno, Tokyo (JP)

(73) Assignee: FUJIFILM TOYAMA CHEMICAL CO., LTD., Tokyo (JP)

( * ) Notice: Subject to any disclaimer, the term of this patent is extended or adjusted under 35 U.S.C. 154(b) by 496 days.

(21) Appl. No.: 15/119,604

(22) PCT Filed: Feb. 17, 2015

(86) PCT No.: PCT/JP2015/054331
§ 371 (c)(1),
(2) Date: Aug. 17, 2016

(87) PCT Pub. No.: WO2015/125790
PCT Pub. Date: Aug. 27, 2015

(65) Prior Publication Data
US 2017/0056289 A1 Mar. 2, 2017

(30) Foreign Application Priority Data
Feb. 18, 2014 (JP) .................................. 2014-043268

(51) Int. Cl.
*A61J 1/16* (2006.01)
*F25B 21/04* (2006.01)
(Continued)

(52) U.S. Cl.
CPC ............ *A61J 1/165* (2013.01); *A01N 1/0252* (2013.01); *A61M 1/0286* (2014.02); *F25B 21/02* (2013.01);
(Continued)

(58) Field of Classification Search
CPC ....... A61J 1/165; A61J 2200/50; F25B 21/04; F25B 21/02; F25B 2700/2106;
(Continued)

(56) References Cited

U.S. PATENT DOCUMENTS 4,838,911 A * 6/1989 Robertson ............... F25B 21/02
62/3.3
5,042,258 A * 8/1991 Sundhar ............. A47G 19/2288
62/3.2
(Continued)

FOREIGN PATENT DOCUMENTS

FR 2994351 A1 * 2/2014
JP 4-332557 A 11/1992
(Continued)

OTHER PUBLICATIONS

International Search Report (PCT/ISA/210) issued in PCT Application No. PCT/JP2015/054331, dated Jun. 2, 2015, with English translation (four (4) pages).
(Continued)

*Primary Examiner* — Steve S Tanenbaum
(74) *Attorney, Agent, or Firm* — Oliff PLC

(57) ABSTRACT

Provided is a compact lightweight transport box in which the internal temperature distribution is minimized and accurate temperature regulation can be performed. The transport box includes an insulating container, an internal heat conducting container mounted in the insulating container, and an insulating cover body with a cover internal side heat conducting plate exposed on an inner surface facing the opening part of the internal heat conducting container, in which, with the opening part of the insulating container closed by the insulating cover body, the cover internal side heat conducting plate is near an opening end of the internal heat conducting container.

13 Claims, 31 Drawing Sheets

(51) Int. Cl.
*F25D 11/00* (2006.01)
*F25D 16/00* (2006.01)
*A01N 1/02* (2006.01)
*F25B 21/02* (2006.01)
*A61M 1/02* (2006.01)

(52) U.S. Cl.
CPC .............. *F25B 21/04* (2013.01); *F25D 11/00* (2013.01); *F25D 11/003* (2013.01); *F25D 16/00* (2013.01); *A61J 2200/50* (2013.01); *A61M 2205/3368* (2013.01); *A61M 2205/3633* (2013.01); *A61M 2205/3673* (2013.01); *A61M 2205/8206* (2013.01); *A61M 2205/8237* (2013.01); *F25B 2321/0212* (2013.01); *F25B 2321/0251* (2013.01); *F25B 2700/2106* (2013.01); *F25B 2700/2107* (2013.01); *F25D 2331/8014* (2013.01); *F25D 2700/14* (2013.01); *F25D 2700/16* (2013.01)

(58) Field of Classification Search
CPC ...... F25B 2700/2107; F25B 2321/0251; F25B 2321/0212; A01N 1/0252; F25D 16/00; F25D 11/003; F25D 11/00; F25D 2700/14; F25D 2700/16; A61M 1/0286; A61M 2205/3673
USPC ........................................................ 62/457.9
See application file for complete search history.

(56) References Cited

U.S. PATENT DOCUMENTS

| | | | | |
|---|---|---|---|---|
| 6,294,721 B1 * | 9/2001 | Oravetz | ................ | H01L 35/02 136/203 |
| 6,666,032 B1 * | 12/2003 | Rickson | ................ | A61J 1/165 62/3.6 |
| RE41,295 E * | 5/2010 | Cauchy | ................ | B60N 3/104 62/3.3 |
| 2008/0155991 A1 * | 7/2008 | Lee | ................ | A42B 3/285 62/3.2 |
| 2009/0038317 A1 * | 2/2009 | Otey | ................ | F25B 21/04 62/3.2 |
| 2010/0000229 A1 * | 1/2010 | Tindale | ................ | F25B 21/02 62/3.6 |
| 2011/0247356 A1 * | 10/2011 | Krosse | ................ | F25B 21/02 62/457.1 |
| 2012/0312030 A1 * | 12/2012 | Lu | ................ | F25B 21/02 62/3.6 |
| 2013/0082519 A1 * | 4/2013 | Nagakura | ............. | H02J 7/0068 307/9.1 |

FOREIGN PATENT DOCUMENTS

| | | |
|---|---|---|
| JP | 9-138047 A | 5/1997 |
| JP | 10-111059 A | 4/1998 |
| JP | 10-300306 A | 11/1998 |
| JP | 2001-157375 A | 6/2001 |
| JP | 2002-282136 A | 10/2002 |
| JP | 2007-139328 A | 6/2007 |
| JP | 2008-86608 A | 4/2008 |
| JP | 2008-286506 A | 11/2008 |
| JP | 2010-62694 A | 3/2010 |

OTHER PUBLICATIONS

Japanese-language Written Opinion (PCT/ISA/237) issued in PCT Application No. PCT/JP2015/054331, dated Jun. 2, 2015 (five (5) pages).

* cited by examiner

FIG. 10

| TRANSPORT BOX | SPACING X (mm) | MEASURING POINT (1) (°C) | MEASURING POINT (2) (°C) | MEASURING POINT (3) (°C) | MEASURING POINT (4) (°C) | MEASURING POINT (5) (°C) | MEASURING POINT (6) (°C) | MEASURING POINT (7) (°C) | MEASURING POINT (8) (°C) | INTERNAL AVERAGE TEMPERATURE (°C) |
|---|---|---|---|---|---|---|---|---|---|---|
| A (COMPARATIVE EXAMPLE 1) | 15 | 25.5 | 2.3 | 4.1 | 4.7 | 4.2 | 4.2 | 9.7 | 4.1 | 3.9 |
| B (COMPARATIVE EXAMPLE 2) | 5 | 25.8 | 2.2 | 4 | 4.5 | 4.1 | 4 | 7.5 | 3.8 | 3.8 |
| C (COMPARATIVE EXAMPLE 3) | −5 | 25.8 | 2.3 | 3.9 | 4.5 | 4 | 3.9 | 6.3 | 3.8 | 3.7 |
| D (COMPARATIVE EXAMPLE 4) | 15 | 25.7 | 2.2 | 3.9 | 4.6 | 4 | 3.9 | 7.6 | 3.9 | 3.7 |
| E (EMBODIMENT 2) | 5 | 25.3 | 2.1 | 3.6 | 4.3 | 3.9 | 4 | (5.5) | 3.6 | 3.6 |
| F (EMBODIMENT 3) | −5 | 25.6 | 2.3 | 3.9 | 4.6 | 4 | 4 | (4.9) | 3.7 | 3.8 |

TEMPERATURE-REGULATED TRANSPORT BOX

TECHNICAL FIELD

The present invention relates to a temperature-regulated transport box which houses an object of transport requiring strict temperature regulation, such as a blood product, and transports it to a required place while regulating its temperature (hereinafter sometimes simply called a transport box).

BACKGROUND ART

A blood product must be strictly temperature-regulated at the stages from purification to blood infusion and its temperature must be regulated and kept in a manner to be divided into a first temperature zone suitable for storage of red blood cells (2-6° C.), a second temperature zone suitable for storage of blood platelets (20-24° C.), and a third temperature zone suitable for storage of frozen plasmas (−20° C. or less).

Therefore, under the condition that the blood product is stored at a fixed temperature, the internal temperature distribution is kept within the above blood product storage temperature range.

In the purifying process for the blood product, the blood product is kept within the storage temperature range using a special refrigerator, but for transportation from a blood center to a hospital, a portable transport box which meets the demand for prolonged accurate temperature regulation without an external power source is not available at present.

For this reason, the use of blood products in a remote place such as an isolated island is limited. Since a ship is used for access to an isolated island, temperature regulation must be performed for several hours without a power source and thus a compact, lightweight and energy-efficient transport box is needed.

Japanese Patent Application Laid-Open No. 2008-86608 (Patent Literature 1, PTL 1) proposes a blood product carrier which uses both a stirling refrigerator and a sheath heater so that the extremely cold air generated in the stirling refrigerator is heated by the sheath heater and it is internally circulated by convection for cold storage of the blood product.

Japanese Patent Application Laid-Open No. 2008-286506 (Patent Literature 2, PTL 2) proposes a storage container which includes an insulating container for storing a housed object at a specified temperature, a temperature sensor for detecting the internal temperature of the insulating container, a plurality of thermo-modules having a Peltier element, a heat absorption side thermal conductor and a heat radiation side thermal conductor, and a control board for driving the thermo-modules according to the result of detection by the temperature sensor and controlling the internal temperature of the insulating container, in which the control board controls the power supplied to the thermos-modules within a prescribed value range.

CITATION LIST

Patent Literature

PTL 1: Japanese Patent Application Laid-Open No. 2008-86608

PTL 2: Japanese Patent Application Laid-Open No. 2008-286506

SUMMARY OF INVENTION

Technical Problem

The carrier in PTL 1 may be heavy and large in size since it houses various members including the stirling refrigerator, sheath heater, and ventilation trunk.

Furthermore, the blood product housed in the carrier interferes with convection of cold air and thus causes an uneven temperature distribution in the carrier, thereby making it difficult to regulate the temperature properly. In addition, the stirling refrigerator is a cold source which has an extremely cold temperature of −20° C. or less, and requires troublesome work such as periodic defrosting.

In the storage container in PTL 2, control is performed on the assumption that the ambient temperature where the storage container is installed is nearly an ordinary temperature and the temperature variation is small.

However, there is a temperature distribution in the storage container and if a thermo-module is installed, for example, near a door, a large temperature difference occurs. The temperature to be controlled is the internal center temperature, and since the internal resistance of the Peltier element changes according to temperature, when the ambient temperature (external air temperature) changes largely, the internal temperature distribution changes and the electric power required to control the internal center temperature to a set temperature changes. Therefore, there arises the problem that an uncontrollable change in the internal temperature cannot be prevented only by detecting the internal temperature.

Furthermore, even in an attempt to detect the internal temperature directly for the purpose of control, it takes time for the temperature of the target area of temperature control to be transmitted to an internal temperature measuring point because of the temperature difference from the temperature of the area where the Peltier element is mounted, so the internal temperature changes largely and the internal temperature cannot be controlled stably.

An object of the present invention is to provide a temperature-regulated transport box in which the internal temperature distribution is minimized and the internal temperature can be accurately regulated even when the ambient temperature changes.

Solution to Problem

In order to achieve the above object, a first invention is characterized by including:

an insulating container having an opening part on one side;

an internal heat conducting container mounted inside the insulating container to house an object of transport;

an insulating cover body with a cover internal side heat conducting layer exposed on an inner surface facing an opening part of the internal heat conducting container, to open and close the opening part of the insulating container; and temperature control means to keep a temperature of an internal space formed by closing the opening part of the insulating container by the insulating cover body, at a prescribed temperature, in which with the opening part of the insulating container closed by the insulating cover body, the cover internal side heat conducting layer of the insulating cover body is near an opening end of the internal heat conducting container.

In order to achieve the above object, a second invention is characterized by including:

an insulating container having an opening part on one side;

an internal heat conducting container mounted inside the insulating container to house an object of transport;

an insulating cover body to open and close the opening part of the insulating container; and temperature control means to keep a temperature of an internal space formed by closing the opening part of the insulating container by the insulating cover body, at a prescribed temperature, the temperature control means including:

an electronic cooling unit having a heat absorption side thermal conductor, a heat radiation side thermal conductor, and a Peltier element interposed between the heat absorption side thermal conductor and the heat radiation side thermal conductor; a power source to supply power to the Peltier element; a power supply control temperature sensor mounted on an outer lateral surface of the internal heat conducting container near a portion in contact with the heat absorption side thermal conductor or on the heat absorption side thermal conductor; an ambient temperature sensor to detect an ambient temperature around the temperature-regulated transport box; and a power supply control board to control an amount of power supplied to the Peltier element according to a detection signal from the power supply control temperature sensor, in which the power supply control board receives the detection signal from the ambient temperature sensor and adjusts a value of current supplied to the Peltier element according to the ambient temperature so as to stabilize the temperature of the internal space at a set temperature.

Advantageous Effects of Invention

The present invention is structured as mentioned above and can provide a temperature-regulated transport box in which the internal temperature distribution is minimized and the internal temperature can be regulated accurately even when the ambient temperature changes.

BRIEF DESCRIPTION OF DRAWINGS

FIG. 10 is a table summarizing temperature measurement results at various points in transport boxes A to F in Comparative Examples 1 to 4 and the second and third embodiments of the present invention.

DESCRIPTION OF EMBODIMENTS

Figure 1:
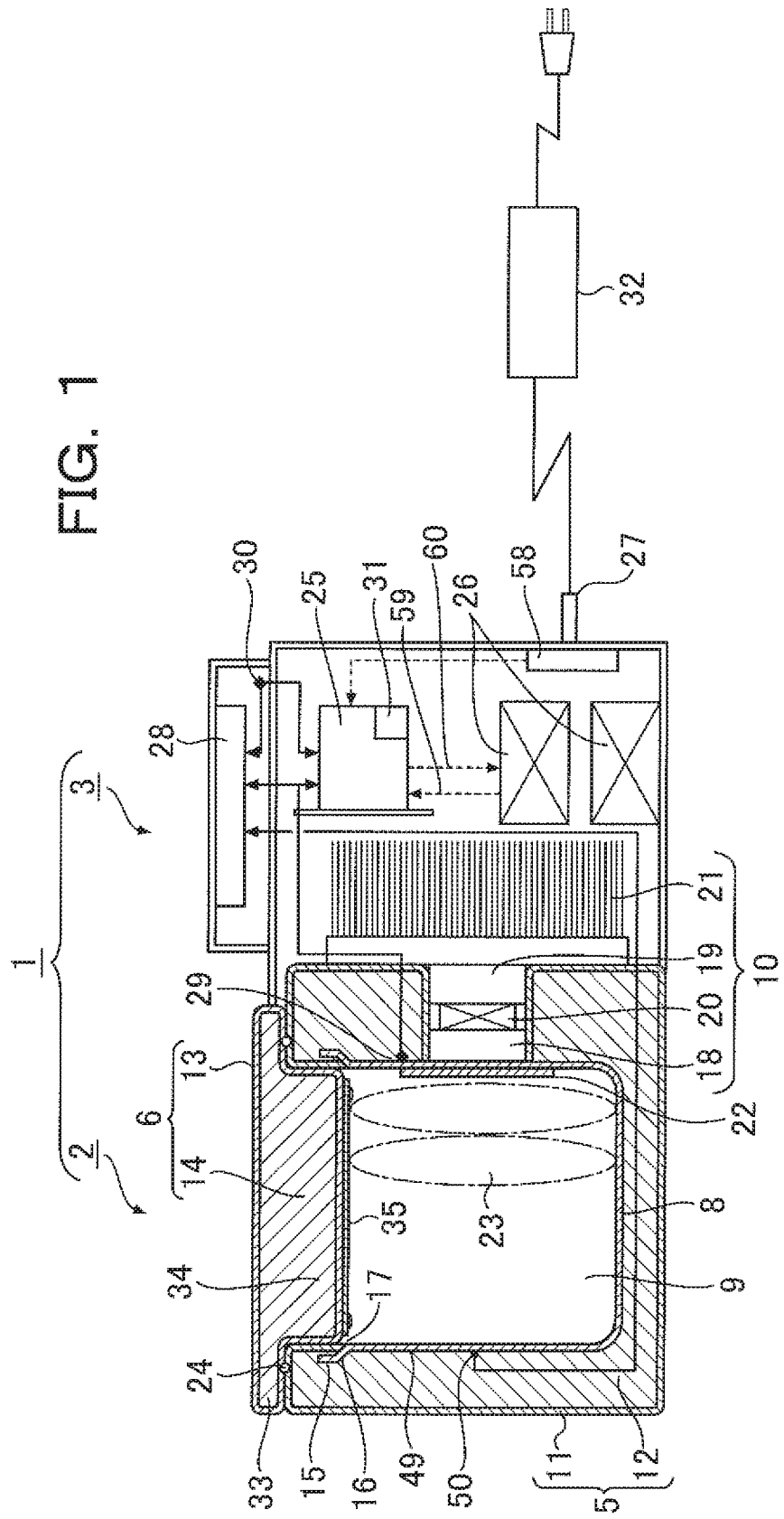
FIG. 1 is a schematic block diagram of a transport box according to a first embodiment of the present invention.
Figure 2:
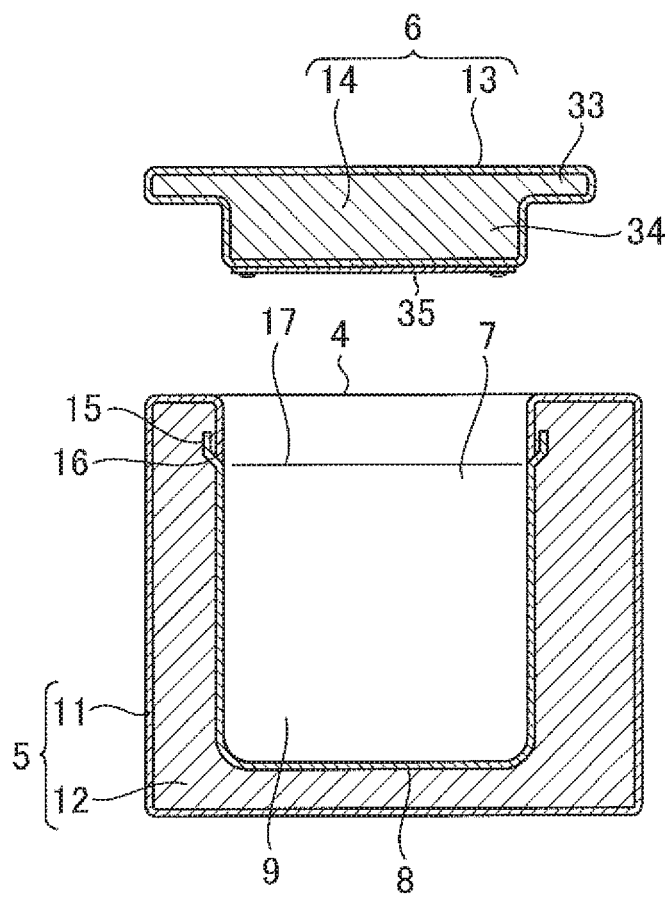
FIG. 2 is a sectional view of the transport box with an insulating container and an insulating cover body separated from each other.
Figure 3:
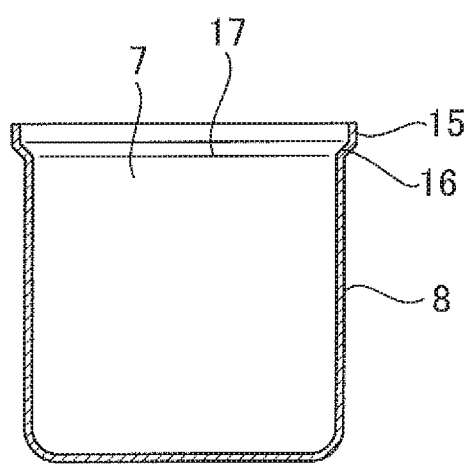
FIG. 3 is a sectional view of an internal heat conducting container used in the transport box.

FIG. 1 is a schematic block diagram of a transport box according to a first embodiment of the present invention, FIG. 2 is a sectional view showing the transport box with an insulating container and an insulating cover body separated from each other, and FIG. 3 is a sectional view of an internal heat conducting container used in the transport box.

As shown in FIG. 1, the transport box 1 includes a box body 2 and a component housing (hereinafter sometimes called the housing) 3 which are adjacent to each other and integrally jointed and almost equal in height.

The box body 2 mainly includes: a box type insulating container 5 (see FIG. 2) with an opening part 4 at the top; an insulating cover body 6 for opening and closing the opening part 4 of the insulating container 5; a box type internal heat conducting container 8 made of aluminum with an alumite-treated surface, having an opening part 7 at the top, which is mounted inside the insulating container 5 in a manner so that the opening part 7 is oriented in the same direction as the opening part 4 of the insulating container 5 (see FIG. 2); and an electronic cooling unit 10 (see FIG. 1) which is in contact with the outer surface of the internal heat conducting container 8 and keeps the temperature of an internal space 9 within a prescribed temperature zone.

The insulating container 5 includes a container casing 11 and a heat insulating material 12 contained in it. The insulating cover body 6 also includes a cover casing 13 and a heat insulating material 14 contained in it.

The heat insulating materials 12 and 14 are, for example, injected hard urethane foam, vacuum heat insulating material, styrene foam or a combination of these. The container casing 11 and cover casing 13 are made of, for example, synthetic resin such as polypropylene or ABS resin, or metal.

As shown in FIG. 3, the upper end 15 of the internal heat conducting container 8 is expanded outward at a curved portion 16 and the upper end 15 (edge) is inside the insulating container 5 (see FIG. 1). The upper end 15 of the internal heat conducting container 8 is located inside the insulating container 5, because if the upper end 15 of the internal heat conducting container 8 is exposed inside the insulating container 5, a vinyl glove worn on a hand to take a blood product out of or into the transport box might be damaged.

Therefore, as shown in FIG. 2, with the internal heat conducting container 8 attached to the insulating container 5, the substantial opening end 17 of the internal heat conducting container 8 which is exposed to the internal surface of the insulating container 5 is the base part of the curved portion 16.

As shown in FIG. 1, the electronic cooling unit 10 includes a heat absorption side thermal conductor 18, a heat radiation side thermal conductor 19, a Peltier element 20 interposed between them, a radiation fin 21 attached to the outside of the heat radiation side thermal conductor 19, and a fan (not shown) for sending cooling air to the radiation fin 21.

In this embodiment, the electronic cooling unit 10 is attached to the outer surface of one sidewall of the internal heat conducting container 8 at a roughly central position in the sidewall height direction. At least the outer circumferential surfaces of the heat absorption side thermal conductor 18 and Peltier element 20 of the electronic cooling unit 10 are surrounded by the insulating container 5.

As shown in FIG. 1, an internal insulating sheet 22 of foamable resin, etc. is attached to the inner surface of the sidewall of the internal heat conducting container 8 to which the electronic cooling unit 10 is attached.

A blood product 23 is contained in the internal space 9 of the internal heat conducting container 8, but if the blood product 23 is in direct contact with the inner surface of the sidewall to which the electronic cooling unit 10 of the internal heat conducting container 8 is attached, the space may be partially too cold. Therefore, attachment of the internal insulating sheet 22 prevents the blood product 23 from becoming locally too cooled.

In FIG. 1, reference sign 24 represents a packing provided at the joint of the insulating container 5 and the insulating cover body 6, which keeps the internal space 9 airtight.

The housing 3 houses components including the radiation fin 21 attached to the electronic cooling unit 10, the fan (not shown) for sending cooling air to the radiation fin 21, a power supply control board 25, one or more internal batteries 26, a plug-in board 58 for a DC jack 27, and a recording/display unit 28 mounted on the upper surface side of the housing 3.

The power supply control board 25 receives a detection signal from a power supply control temperature sensor 29 mounted near the area where the electronic cooling unit 10 of the internal heat conducting container 8 is mounted, and thereby controls the amount of power supplied to the electronic cooling unit 10.

In this embodiment, the power supply control temperature sensor 29 is mounted near the area where the electronic cooling unit 10 of the internal heat conducting container 8 is mounted; however, the power supply control temperature sensor 29 may be mounted on the heat absorption side thermal conductor 18 of the electronic cooling unit 10.

A detection signal from the ambient temperature sensor 30 mounted in the housing 3 which allows an air flow is sent to the power supply control board 25 and the recording/display unit 28 together with sampling time.

The power supply control board 25 includes a polarity inversion control section 31 for switching the polarity (plus/minus) of voltage to the Peltier element 20 so that the polarity inversion control section 31 prevents an excessive drop in the internal temperature and keeps the internal temperature within the temperature range for the blood product 23 by switching the polarity of power to the Peltier element 20 to heat the internal heat conducting container 8 before the internal temperature becomes lower than the lower limit of the temperature zone.

A secondary battery such as a lithium-ion battery is used as the internal battery 26 and driving is done during transportation of the blood product 23 by power supply 59 from the internal battery 26. In this embodiment, a spare internal battery 26 is also mounted.

An AC adaptor 32 is connected to the DC jack 27 and an external power source (AC power source or a vehicle's power source) becomes available by insertion of the DC jack 27 into the plug-in board 58. If the transport box 1 is used at a hospital or the like, for example, as a cool box, charging 60 of the internal battery 26 is done by supplying power to the Peltier element 20, etc. from the external power source (AC power source).

As the DC jack 27 is pulled out of the plug-in board 58, charging 60 of the internal battery 26 is stopped and switching is automatically done to power supply 59 from the internal battery 26 to the power supply control board 25.

As shown in FIG. 1, the internal heat conducting container 8 contains the blood product 23 and the internal temperature of the internal heat conducting container 8 is kept within the first temperature zone (2-6° C.) suitable for storage of red blood cells or within the second temperature zone (20-24° C.) suitable for storage of platelets by internal temperature control means which includes the electronic cooling unit 10 (Peltier element 20), power source (built-in internal battery 26, external power source), temperature sensors 29 and 30, and power supply control board 25.

The internal heat conducting container 8 is mounted inside the insulating container 5 in a manner that the opening part 7 is oriented in the same direction (upward in this embodiment) as the opening part 4 of the insulating container 5. The opening end 17 of the internal heat conducting container 8 (in this embodiment, the lower base part of the curved portion 12 is substantially the opening end 17) is located more inward (downward) than the opening end of the insulating container 5.

The insulating cover body 6 has a flange 33 having almost the same shape and area as the upper surface of the insulating container 5 at its top and an inwardly protruding portion 34 protruding inward (downward) from the flange 33, which are integrally formed. The insulating cover body 6 is supported by a hinge structure (not shown) near the opening part of the insulating container 5 in an openable/closable manner.

A cover internal side heat conducting plate 35 as an aluminum plate whose surface is alumite-treated is fixed on the lower (inner) surface of the inwardly protruding portion 34. The lower surface of the cover internal side heat conducting plate 35 is exposed without being covered by another member so that radiation cooling (see FIG. 12) by heat radiation 43 is performed effectively.

The area of the cover internal side heat conducting plate 35 is almost the same as the area of the opening part 7 of the internal heat conducting container 8. Therefore, as shown in FIG. 1, with the opening part 4 of the insulating container 5 closed by the insulating cover body 6, the periphery of the cover internal side heat conducting plate 35 is near the opening end 17 of the internal heat conducting container 8 and the lower surface of the cover internal side heat conducting plate 35 is roughly in the same position as the opening end 17 of the internal heat conducting container 8 or in a slightly more inward position than the opening end 17 of the internal heat conducting container 8 (see FIG. 1).

As shown in FIG. 1, an internal temperature display temperature sensor 50 is mounted in a position of the internal heat conducting container 8 where a temperature nearer to the temperature of the blood product 23 in cold storage (equivalent temperature) can be detected. A detection signal from the internal temperature display temperature sensor 50 is sent to the recording/display unit 28 and recorded together with sampling time as management data for the blood product 23.

The position of the internal temperature display temperature sensor 50 is predetermined on the basis of an experiment and in this embodiment, it is mounted on an opposite sidewall 49 opposite to the sidewall to which the electronic cooling unit 10 of the internal heat conducting container 8 is attached.

Figure 6:
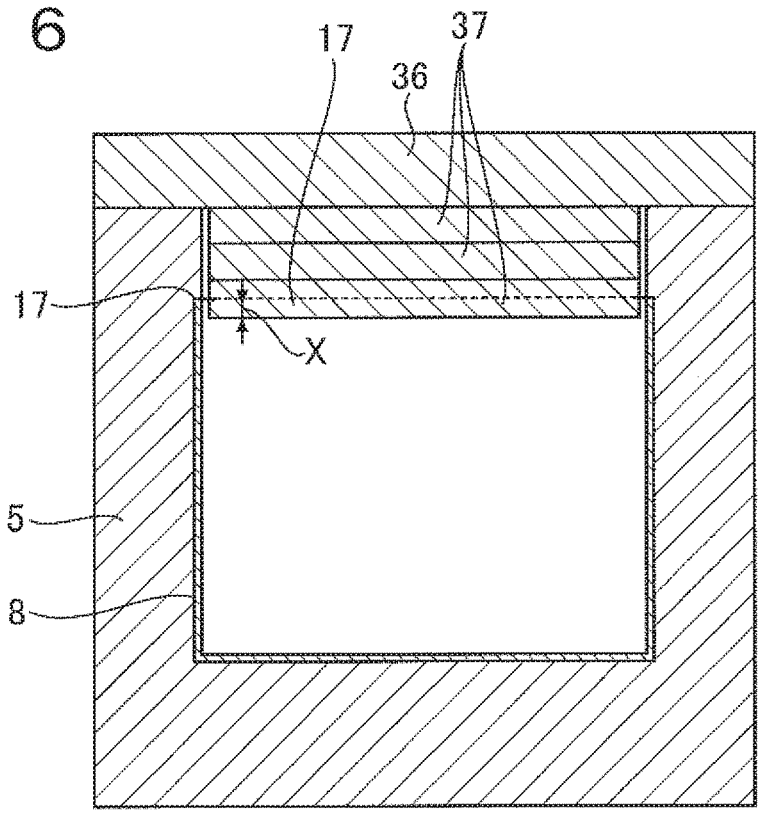
FIG. 6 is a sectional view of a transport box according to Comparative Example 3.
Figure 7:
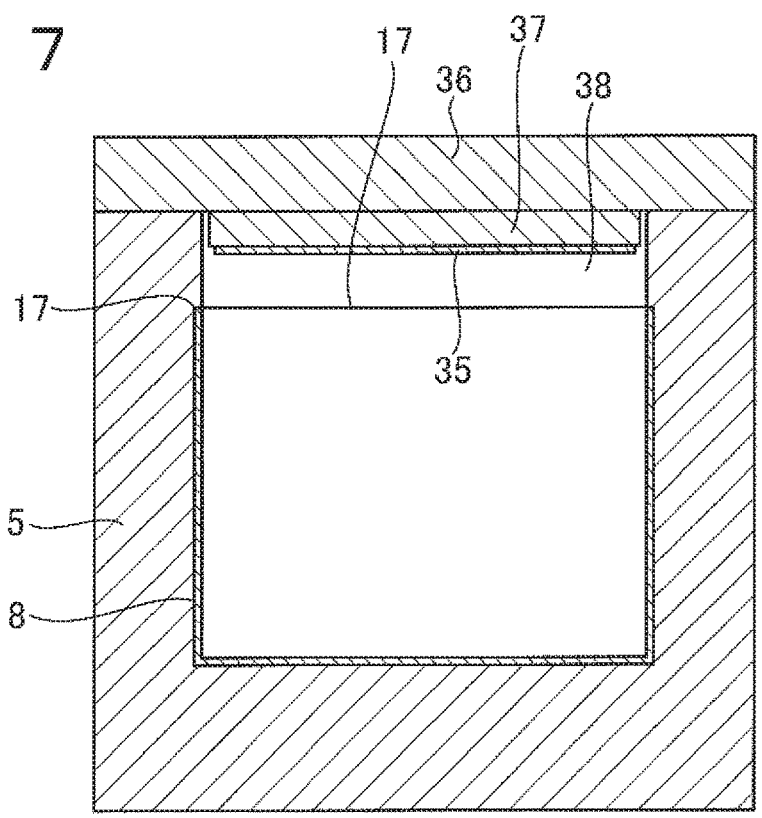
FIG. 7 is a sectional view of a transport box according to Comparative Example 4.
Figure 8:
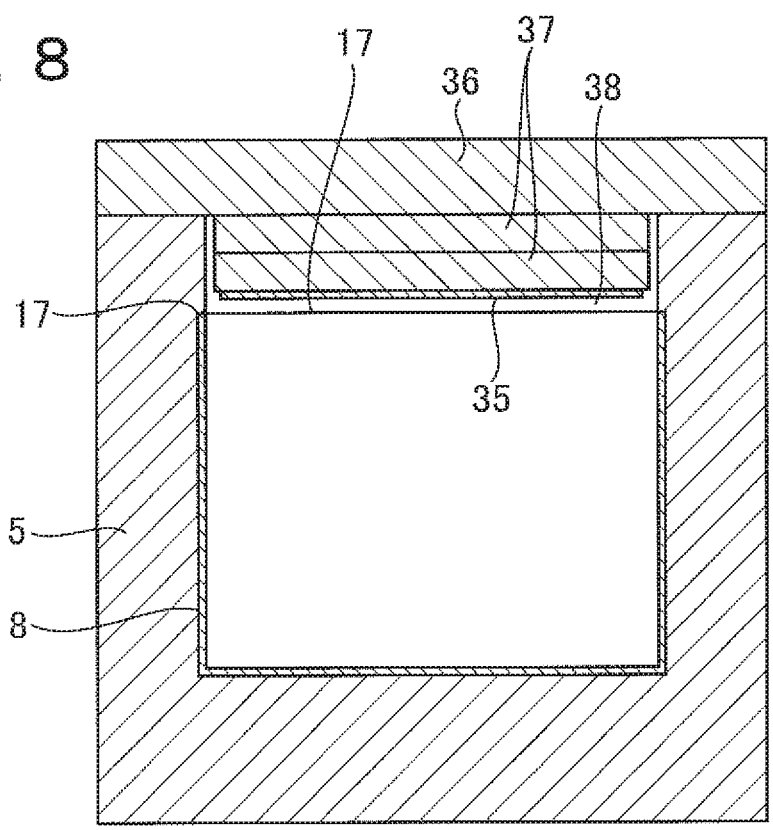
FIG. 8 is a sectional view of a transport box according to a second embodiment of the present invention.
Figure 9:
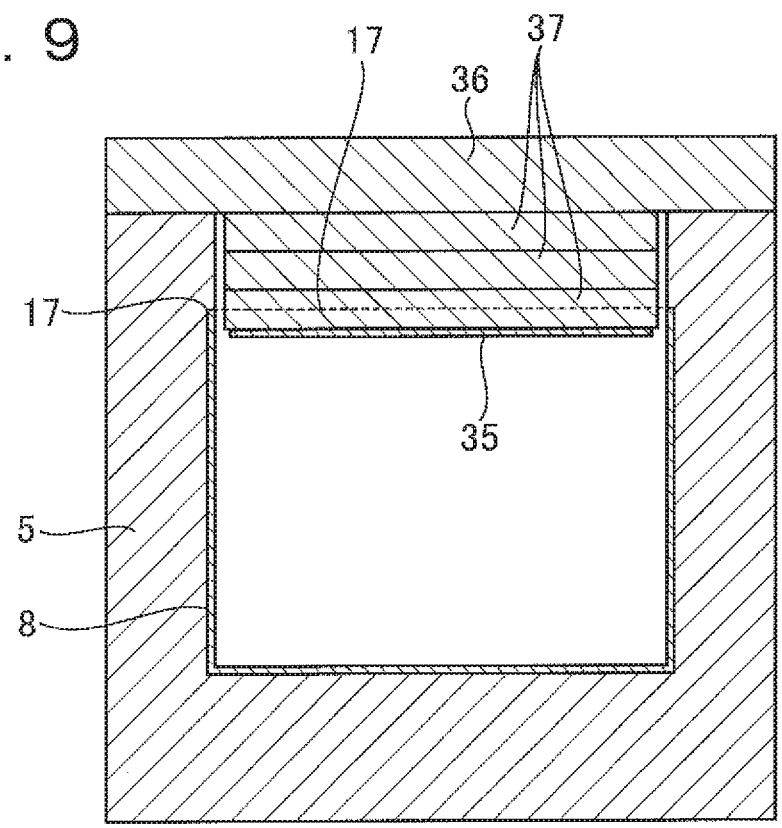
FIG. 9 is a sectional view of a transport box according to a third embodiment of the present invention.

FIGS. 4 to 7 are sectional views of transport boxes according to Comparative Examples 1 to 4 and FIGS. 8 and 9 are sectional views of transport boxes according to second and third embodiments of the present invention. In all the examples, the internal heat conducting container 8 is attached to the inside of the insulating container 5 and the opening end 17 of the internal heat conducting container 8 is in a lower position than the opening end of the insulating container 5. The opening part 4 of the insulating container 5 is closed by a flat insulating cover plate 36.

In all the examples, the insulating container 5 and the internal heat conducting container 8 are the same in terms of shape and size and the electronic cooling unit 10 (not shown) is attached to the outside of the internal heat conducting container 8, but the condition of the insulating cover body 6 varies among the examples.

Figure 4:
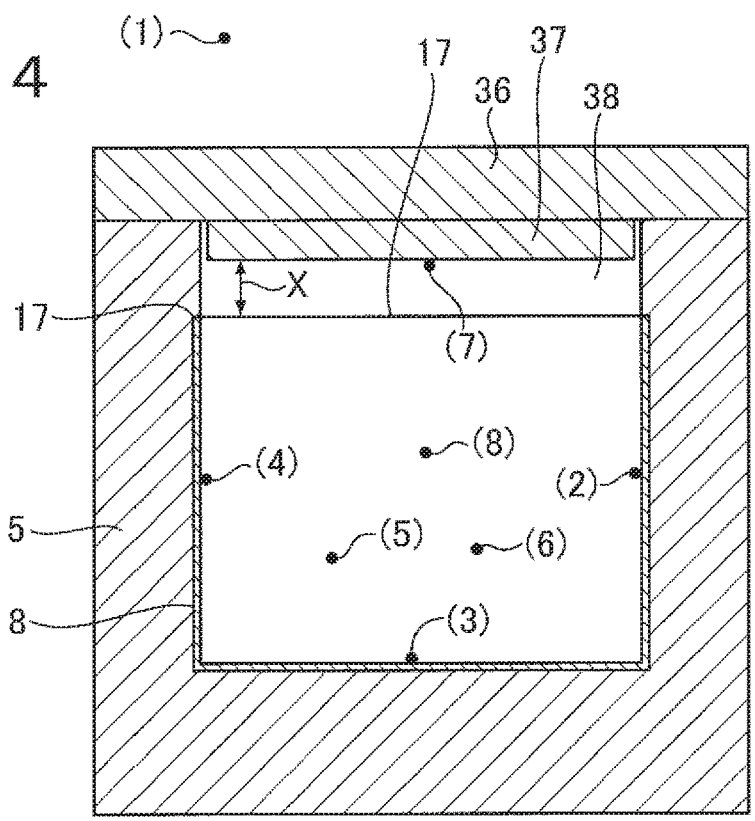
FIG. 4 is a sectional view of a transport box according to Comparative Example 1.

In the transport box A in Comparative Example 1 shown in FIG. 4, one cover internal side insulating plate 37 with a thickness of 10 mm is mounted on the lower surface of the insulating cover plate 36 and spacing X from the opening end 17 of the internal heat conducting container 8 to the lower surface of the cover internal side insulating plate 37 is 15 mm and a relatively thick space 38 is formed between them. In all the examples, the area of the cover internal side insulating plate 37 is the same.

Figure 5:
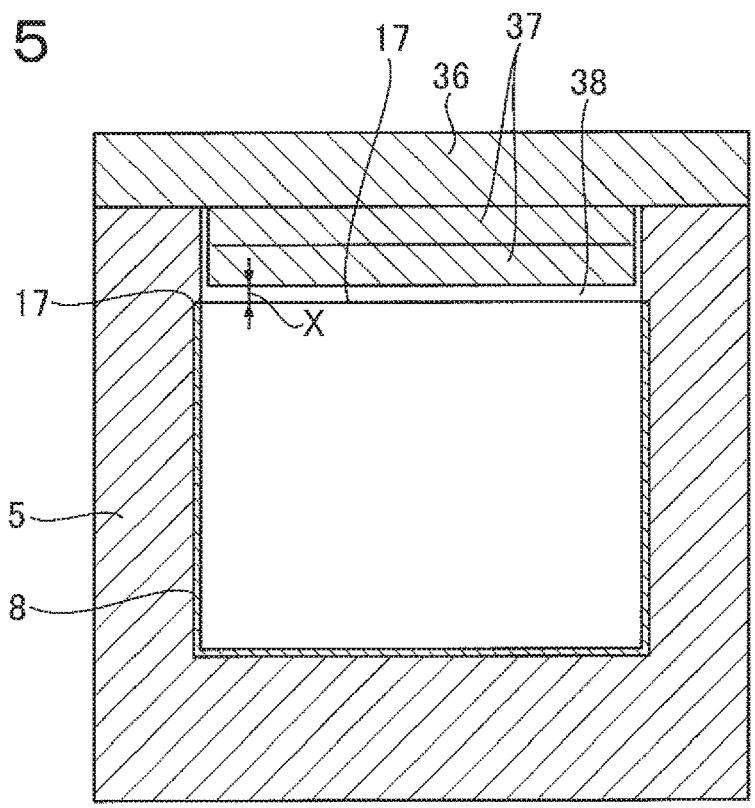
FIG. 5 is a sectional view of a transport box according to Comparative Example 2.

In the transport box B in Comparative Example 2 shown in FIG. 5, two cover internal side insulating plates 37 with a thickness of 10 mm are stacked on the lower surface of the insulating cover plate 36 and spacing X from the opening end 17 of the internal heat conducting container 8 to the lower surface of the lowest cover internal side insulating plate 37 is 5 mm and a space 38 with a thickness of 5 mm is formed between them.

In the transport box C in Comparative Example 3 shown in FIG. 6, three cover internal side insulating plates 37 with a thickness of 10 mm are stacked on the lower surface of the insulating cover plate 36 and the lower half of the lowest cover internal side insulating plate 37 (5 mm in thickness) is in the opening part 7 of the internal heat conducting container 8 and spacing X from the opening end 17 of the internal heat conducting container 8 to the lower surface of the lowest cover internal side insulating plate 37 is −5 mm. Therefore, in Comparative Example 3, and a space 38 is not formed between the opening end 17 of the internal heat conducting container 8 and the lower surface of the lowest cover internal side insulating plate 37.

In the transport box D in Comparative Example 4 shown in FIG. 7, a cover internal side heat conducting plate 35 as a 2 mm-thick aluminum plate with an alumite-treated surface is attached to the lower surface of the cover internal side insulating plate 37 of the transport box A shown in FIG. 4.

In the transport box E in the second embodiment shown in FIG. 8, the same cover internal side heat conducting plate 35 is attached to the lower surface of the lowest cover internal side insulating plate 37 of the transport box B shown in FIG. 5.

In the transport box F in the third embodiment shown in FIG. 9, the same cover internal side heat conducting plate 35 is attached to the lower surface of the lowest cover internal side insulating plate 37 of the transport box C shown in FIG. 6 and the lower half of the lowest cover internal side insulating plate 37 and the cover internal side heat conducting plate 35 are inside the opening part 7 of the internal heat conducting container 8.

As shown in FIG. 4, measuring point (1) is a temperature measuring point for the outside of the transport box; measuring point (2) is a temperature measuring point for the inner surface to which the electronic cooling unit 10 of the internal heat conducting container 8 is attached; measuring point (3) is a temperature measuring point for the inner bottom surface of the internal heat conducting container 8; measuring point (4) is a temperature measuring point opposite to the measuring point (2) for the internal heat conducting container 8; measuring point (5) is a temperature measuring point for the right side surface (side surface on the nearer side in the figure) of the internal heat conducting container 8; measuring point (6) is a temperature measuring point for the left side surface (side surface on the farther side in the figure) of the internal heat conducting container 8; measuring point (7) is a temperature measuring point for the lower surface of the cover internal side insulating plate 37 or the cover internal side heat conducting plate 35; and measuring point (8) is a temperature measuring point for the center of the internal space.

FIG. 10 summarizes the results of temperature measurement at the measuring points (1) to (8) in the transport boxes A to F shown in FIGS. 4 to 9. This figure also shows the results of calculation of the average temperatures of the internal heat conducting surfaces of the transport boxes A to F as internal average temperatures.

Figure 11:
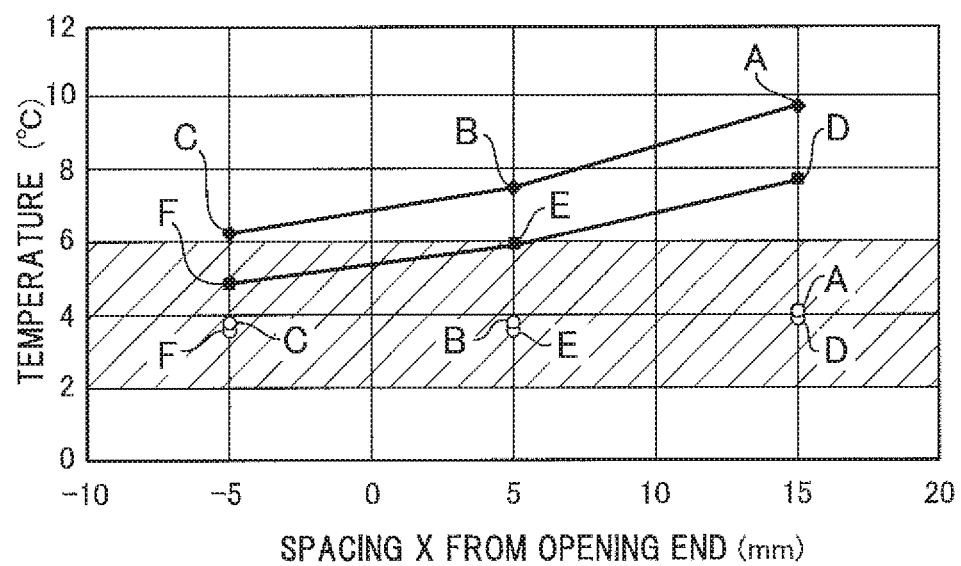
FIG. 11 is a characteristic graph showing the relation between spacing X from the opening end of the internal heat conducting container to the lower surface of the cover internal side insulating plate, and the measured temperature of the lower surface of the cover internal side insulating plate or the cover internal side heat conducting plate and the measured internal center temperature in the transport boxes A to F.

FIG. 11 is a characteristic graph showing the relation between spacing X from the opening end 17 of the internal heat conducting container 8 to the lower surface of the cover internal side insulating plate 37, and the measured temperature of the lower surface (measuring point 7) of the cover internal side insulating plate 37 or the cover internal side heat conducting plate 35 and the measured internal center temperature (measuring point 8).

In the figure, ♦ (diamond shape) A represents the measured temperature of the lower surface of the cover internal side insulating plate of the transport box A, ♦ (diamond shape) B represents that of the transport box B and ♦ (diamond shape) C represents that of the transport box C. ■ (square shape) D represents the measured temperature of the lower surface of the cover internal side heat conducting plate of the transport box D, ■ (square shape) E represents that of the transport box E and ■ (square shape) F represents that of the transport box F.

○ (circular shape) A represents the measured internal center temperature of the transport box A, ○ (circular shape) B represents that of the transport box B, ○ (circular shape) C represents that of the transport box C, ○ (circular shape) D represents that of the transport box D, ○ (circular shape) E represents that of the transport box E, and ○ (circular shape) F represents that of the transport box F.

The temperature region in the shaded area of FIG. 11 indicates the first temperature zone (2-6° C.) suitable for storage of red blood cells. The transport boxes used in this test use urethane foam resin as a heat insulating material and its average thickness is 25 mm, the internal volume is 2.3 L, the internal dimensions are W: 140 mm, D: 110 mm, and H: 160 mm. Temperature measurements at the various points were made by thermocouples.

As apparent from the results shown in FIGS. 10 and 11, in the transport box A shown in FIG. 4, the distance from the lower surface of the cover internal side insulating plate 37 to the opening end 17 of the internal heat conducting container 8 is as large as 15 mm and the thick space 38 exists between them, so even when the internal space is cooled by the electronic cooling unit 10, the temperature of the lower surface (measuring point 7) of the cover internal side insulating plate 37 is the highest at 9.7° C. or 5.6° C. higher than the internal center temperature (measuring point 8).

If the thickness of the cover internal side insulating plate 37 is increased toward the internal heat conducting container 8 as in the transport boxes B and C shown in FIGS. 5 and 6, or if the cover internal side heat conducting plate 35 is added to the transport box A as in the transport box D shown in FIG. 7, the temperature of the lower surface of the cover internal side insulating plate 37 or the temperature of the lower surface of the cover internal side heat conducting plate 35 tends to decrease but it is higher than the upper limit (6° C.) of the first temperature zone.

Therefore, when the blood product 23 in the transport box is in contact with the lower surface of the cover internal side insulating plate 37 or the lower surface of the cover internal side heat conducting plate 35, the blood product 23 cannot be kept within the first temperature zone suitable for storage of red blood cells.

On the other hand, when the thickness of the cover internal side insulating plate 37 is somewhat thick and the cover internal side heat conducting plate 35 attached to the lower surface of the cover internal side insulating plate 37 is located near the opening end 17 of the internal heat conducting container 8 as in the transport boxes E and F (second and third embodiments) shown in FIGS. 8 and 9, the temperature of the lower surface of the cover internal side heat conducting plate 35 is surely kept within the first temperature zone (2-6° C.) suitable for storage of red blood cells and the temperature difference from the internal center temperature (measuring point 8) is approximately 2° C. or less.

In the transport boxes E and F according to the embodiments, as shown in FIG. 10, all the temperatures at the electronic cooling unit mounting surface of the internal heat conducting container 8 (measuring point 2), the inner bottom surface of the internal heat conducting container 8 (measuring point 3), the surface opposite to the electronic cooling unit mounting surface of the internal heat conducting container 8 (measuring point 4), the right side surface of the internal heat conducting container 8 (measuring point 5), the left side surface of the internal heat conducting container 8 (measuring point 6), the lower surface of the cover internal side heat conducting plate 35 (measuring point 7) and the center of the internal space (measuring point 8) can be surely kept within the first temperature zone (2-6° C.) suitable for storage of red blood cells.

Figure 12:
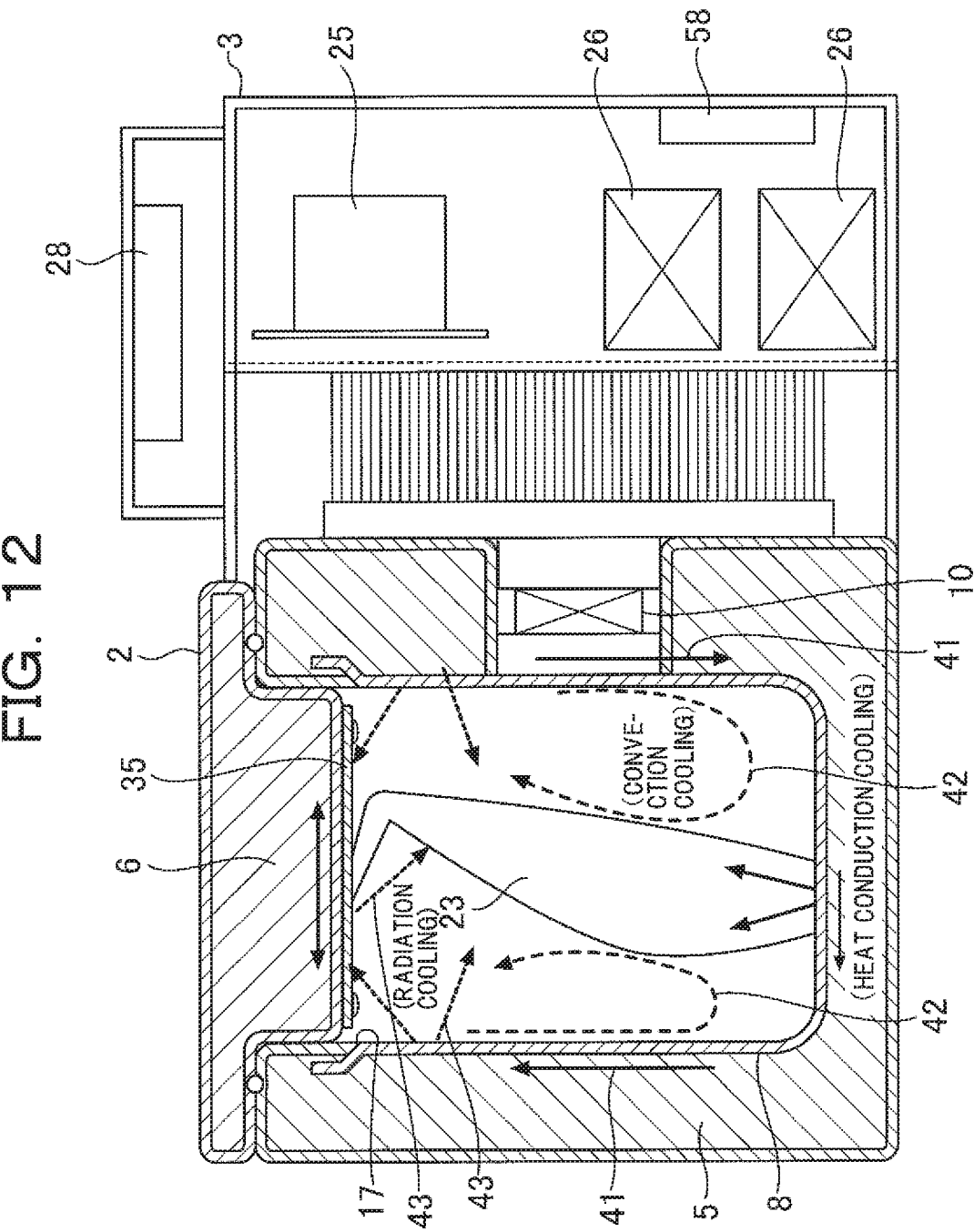
FIG. 12 is a conceptual diagram illustrating the internal heat uniformity of a transport box according to the second and third embodiments of the present invention.

FIG. 12 is a conceptual diagram illustrating the internal heat uniformity of a transport box according to an embodiment.

The transport box includes the insulating container 5 having the internal heat conducting container 8 on the inner surface and the insulating cover body 6 having the cover internal side heat conducting plate 35 on the inner surface and the internal heat conducting container 8 and cover internal side heat conducting plate 35 are made of a material with a high thermal conductivity and a high thermal radiation factor (aluminum with an alumite-treated surface in the embodiments).

The cover internal side heat conducting plate 35 is near the opening end 17 of the internal heat conducting container 8, namely the lower surface (inner surface) of the cover internal side heat conducting plate 35 is just above the opening end 17 of the internal heat conducting container 8 (FIG. 8) or it is almost in the same position as the opening end 17 (FIG. 1), or it is slightly inward from the opening end 17 (FIG. 9) and the periphery of the cover internal side heat conducting plate 35 is near the opening end 17 of the internal heat conducting container 8.

Therefore, the entire internal heat conducting container 8 is uniformly and efficiently cooled by three types of cooling function, namely heat conduction cooling (indicated by solid line) by heat conduction 41 of the internal heat conducting container 8, convection cooling (indicated by long dotted line) by convection 42 of internal air in contact with the internal heat conducting container 8, and radiation cooling (indicated by short dotted line) by heat radiation 43 from the surface of the internal heat conducting container 8.

On top of that, the cover internal side heat conducting plate 35 receives heat radiation 43 from the surface of the internal heat conducting container 8 efficiently, so thermal homogenization is quickly achieved by thermal conductivity of the cover internal side heat conducting plate 35 itself.

Consequently, the entire internal space including the blood product 23 can be thermally homogenized. Furthermore, even when the amount of insertion of the insulating cover body 6 into the insulating container 5 is small, cooling efficiency is high and thermal homogenization can be achieved. Consequently, the available internal volume is larger, so the transport box can be lightweight and compact and a high energy saving effect can be achieved.

Figure 13:
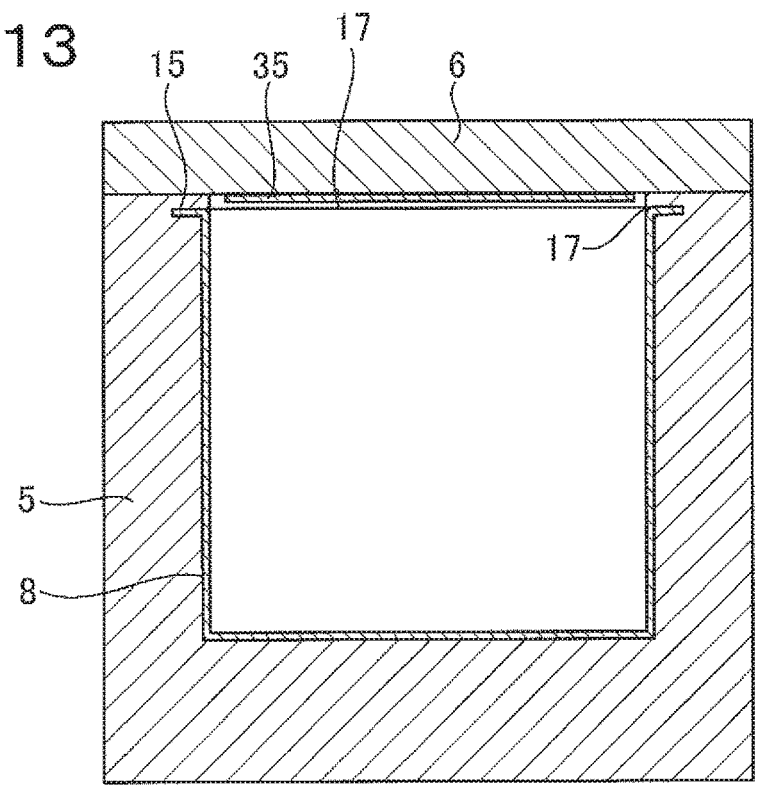
FIG. 13 is a sectional view of a transport box according to a fourth embodiment of the present invention.

FIG. 13 is a sectional view of a transport box according to a fourth embodiment.

This embodiment uses a flat insulating cover body 6 without an inwardly protruding portion 35, in which a cover internal side heat conducting plate 35 is fixed on its inner surface. With the opening part of the insulating container 5 closed by the insulating cover body 6, the cover internal side heat conducting plate 35 is near the opening end 17 of the internal heat conducting container 8, namely the lower surface (inner surface) of the cover internal side heat conducting plate 35 is just above the opening end 17 of the internal heat conducting container 8 (FIG. 8) or it is almost in the same position as the opening end 17 (FIG. 1), or it is located slightly inward from the opening end 17 (FIG. 9).

Figure 14:
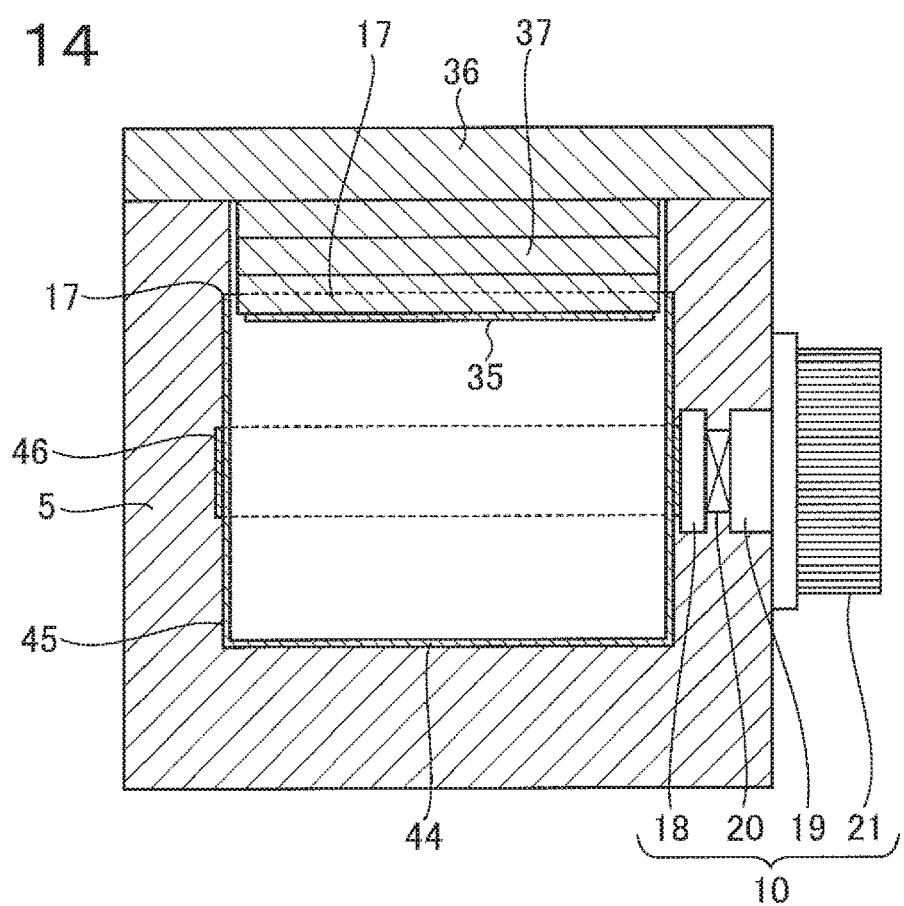
FIG. 14 is a sectional view of a transport box according to a fifth embodiment of the present invention.

FIG. 14 is a sectional view of a transport box according to a fifth embodiment.

The difference of this embodiment from the embodiment shown in FIG. 1 is that a plate-like heat pipe 46 is attached in a manner to surround the outer circumferential surface of the four sidewalls 45 extending in the same direction from the periphery of the bottom 44 of the internal heat conducting container 8 and an electronic cooling unit 10 is attached to a portion of the heat pipe 46.

In this embodiment, the heat pipe 46 is attached in a manner to surround the four sidewalls 45 of the internal heat conducting container 8; however, instead, the heat pipe 46 may be attached in a manner to surround, for example, three sidewalls 45. In this embodiment, the electronic cooling unit 10 contacts the internal heat conducting container 8 indirectly through the heat pipe 46.

If the size of the transport box 1 is increased, thermal homogenization is hardly achieved only by heat conduction of the internal heat conducting container 8 and the weight is heavier. Therefore, due to the presence of the heat pipe 46 between the internal heat conducting container 8 and the electronic cooling unit 10, thermal homogenization by the internal heat conducting container 8 and cover internal side heat conducting plate 35 is made more reliably and more quickly (even after a rapid change in the external air temperature, thermal homogenization is made quickly without causing temperature deviation) and the internal temperature distribution can be improved. In addition, the need for the internal insulating sheet 22 is eliminated.

Although FIGS. 8, 9, and 14 show that the insulating cover plate 36 and a plurality of cover internal side insulating plates 37 are laminated, actually the insulating cover plate 36 and cover internal side insulating plates 37 are integrally formed and used as an insulating cover body 6.

Figure 15:
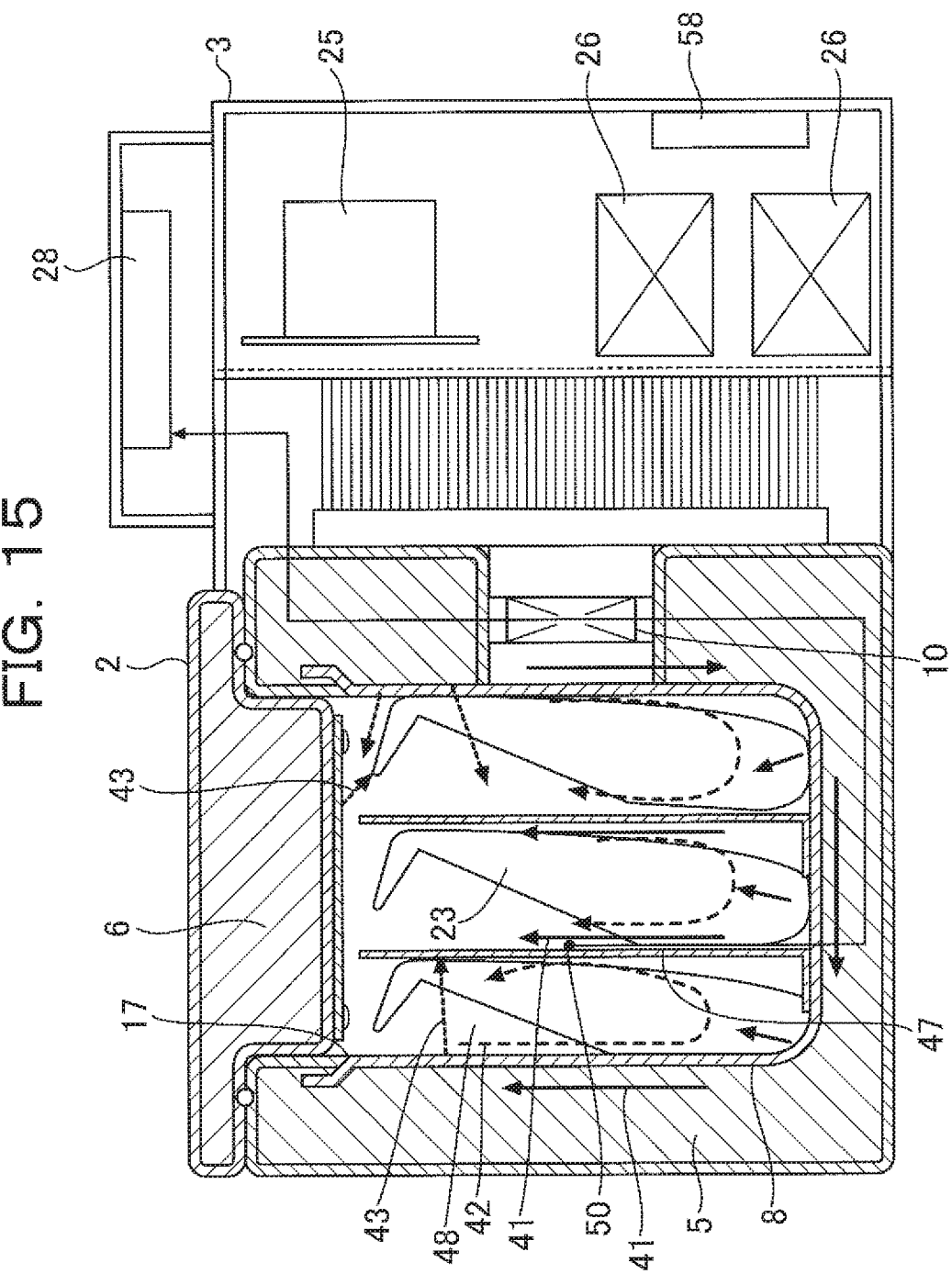
FIG. 15 is a sectional view of a transport box according to a sixth embodiment of the present invention.

FIG. 15 is a sectional view of a transport box according to a sixth embodiment.

In this embodiment, the inside of the internal heat conducting container 8 is partitioned into several spaces by partitioning members 47 to form separate housing spaces 48 for housing the blood product 23 separately. The partitioning members 47 are also made from a 2 mm-thick aluminum plate with an alumite-treated surface.

As shown in FIG. 15, with the insulating cover body 6 closed, the inner surface of the cover internal side heat conducting plate 35 is near the upper ends of the partitioning members 47 and the partitioning members 47 also function as cooling members for the blood product 23.

Specifically, the entire internal heat conducting container 8 is uniformly and efficiently cooled by three types of cooling function: cooling by heat conduction 41 of the partitioning members 47, cooling by convection 42 of air in the space in contact with the partitioning members 47, and cooling by heat radiation 43 from the surfaces of the partitioning members 47.

An internal temperature display temperature sensor 50 is mounted at the position of the partitioning members 47 where a temperature nearer to the temperature of the blood product 23 in cold storage (equivalent temperature) can be detected and a detection signal is sent to the recording/display unit 28 and recorded as management data for the blood product 23.

The position of the partitioning member 47 where the internal temperature display temperature sensor 50 is mounted is determined on the basis of an experiment and in this embodiment, it is mounted on the side surface of the partitioning member 47 located near the center of the internal heat conducting container 8.

Figure 16:
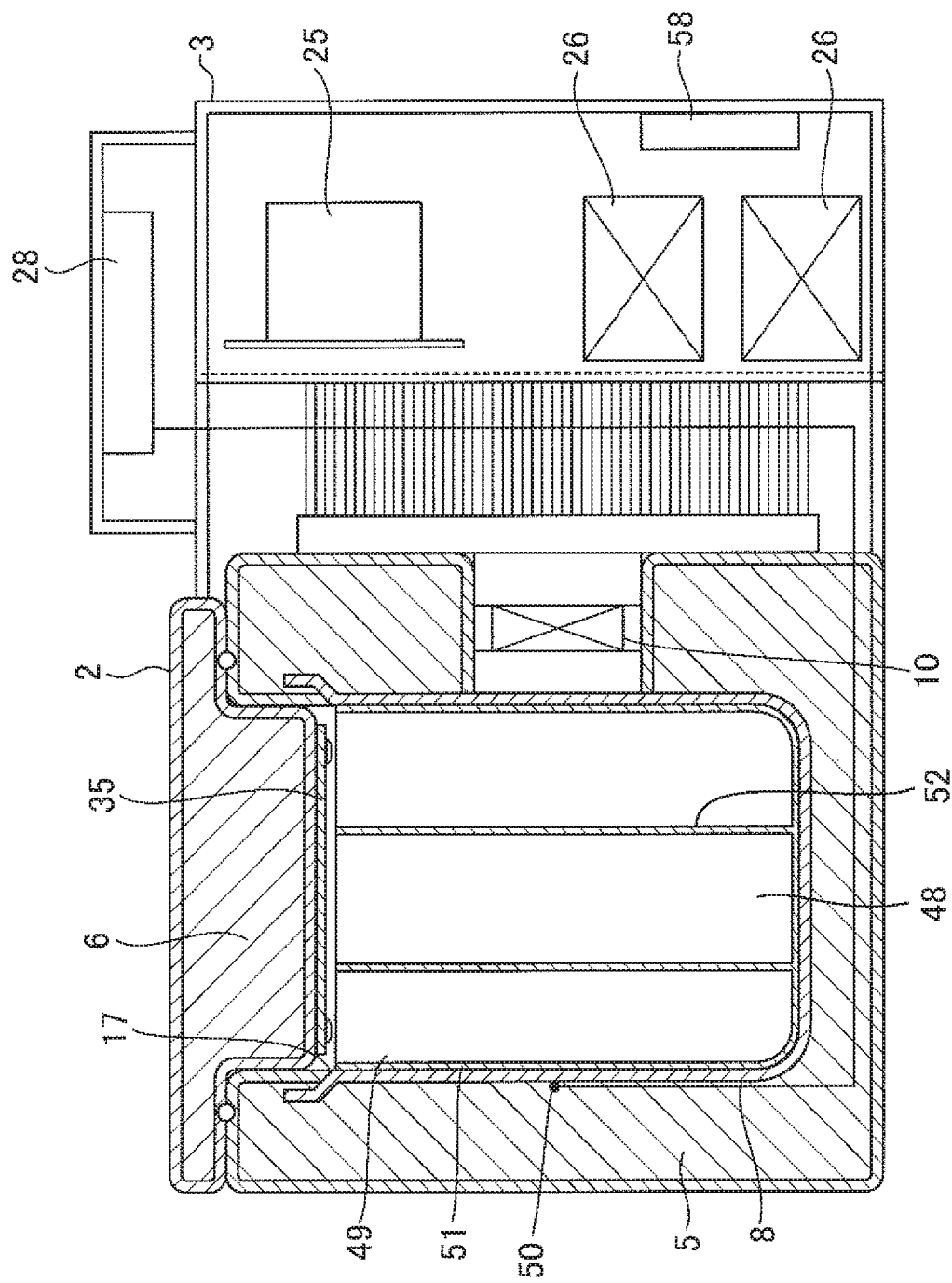
FIG. 16 is a sectional view of a transport box according to a seventh embodiment of the present invention.
Figure 17:
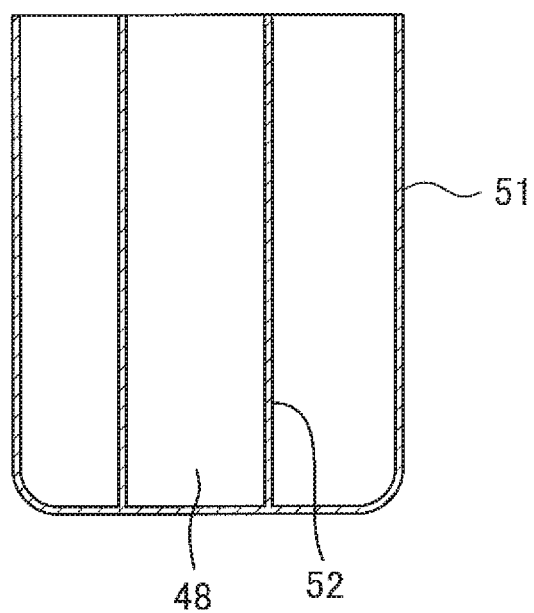
FIG. 17 is a sectional view of a rack used in the transport box.

FIG. 16 is a sectional view of a transport box according to a seventh embodiment and FIG. 17 is a sectional view of a rack.

The difference of this embodiment from the sixth embodiment shown in FIG. 15 is that a rack 51 is used instead of the partitioning members 47. The rack 51 is also made of aluminum with an alumite-treated surface.

The rack 51 has the same outer form as the inner form of the internal heat conducting container 8 in terms of shape and size and is attached into the internal heat conducting container 8 in a detachable manner. A plurality of partitions 52 are provided inside the rack 51 to form a plurality of separate housing spaces 48 for housing the blood product 23 separately.

With the insulating cover body 6 closed, the lower surface of the cover internal side heat conducting plate 35 is near the upper end of the rack 51 and the rack 51 also functions as a cooling member for the blood product 23.

In this embodiment, the internal temperature display temperature sensor 50 is mounted on the opposite sidewall 49 of the internal heat conducting container 8 (see FIG. 16).

Since the rack 51 is detachable from the internal heat conducting container 8, it is convenient to clean the internal heat conducting container 8 and the rack 51.

When storing blood products 23 in the transport box, by first putting a plurality of blood products 23 in the rack 51 and then attaching the rack 51 into the internal heat conducting container 8, conveniently the blood products 23 can be stored simultaneously.

By using the partitioning members 47 or rack 51 as in the sixth or seventh embodiment, all the blood products 23 can be uniformly cooled without causing the blood products 23 to contact or overlap each other in the transport box.

In addition, the blood products 23 are housed separately in an upright position in the transport box, the blood products 23 can be easily taken out of the transport box.

In the sixth and seventh embodiments, the partitioning members 47 and the rack 51 function as cooling members and thereby contribute to thermal homogenization in the transport box, so the cover internal side heat conducting plate 35 may be eliminated.

Figure 18:
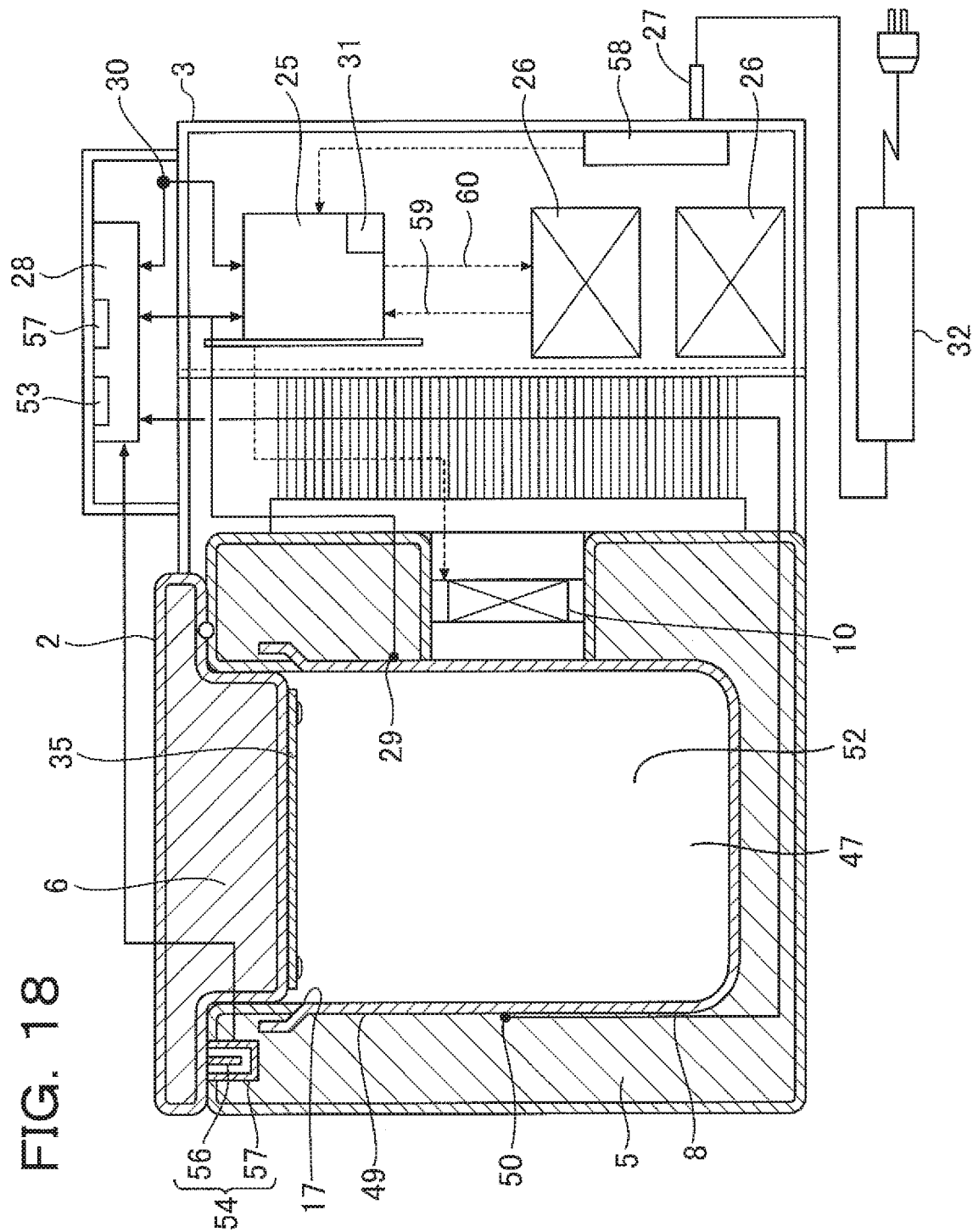
FIG. 18 is a sectional view of a transport box according to an eighth embodiment of the present invention.

FIG. 18 is a sectional view of a transport box according to an eighth embodiment.

For management of the blood product, it is necessary that the storage temperature data for the blood product can be picked out and managed so that whether or not the blood product temperature is properly regulated can be externally checked when the blood product is sent back to the blood center.

In this embodiment, the recording/display unit 28 which records storage temperature data in the period from the start of blood product transport up to the present together with time data includes an external access section 53 such as a USB terminal, USB memory or wireless data transceiver.

A blood product is associated with the safety of human lives and in deciding whether it is properly managed, information, including specific information on a blood product stored in a transport box, ID information on the operator who stored it, specific information on a blood product taken out of the box and ID information on the operator who took it out, is important.

Figure 36:
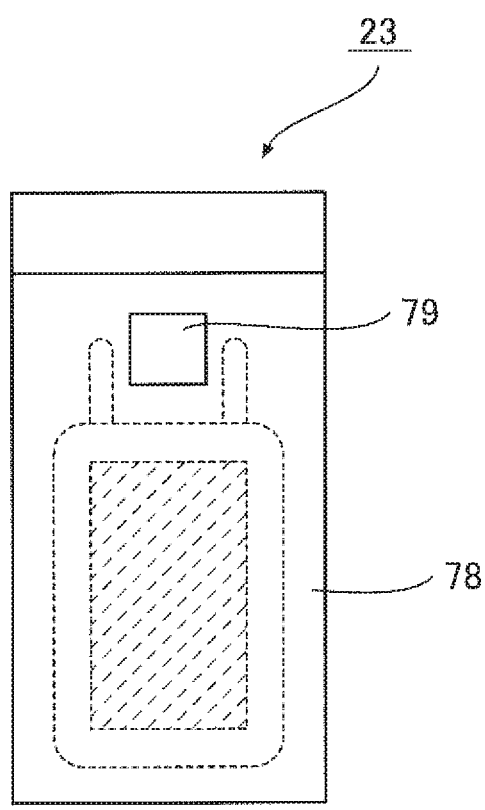
FIG. 36 is a figure of a blood product.

As shown in FIG. 36, an IC tag 79 which stores blood product information such as specific information on the blood product is attached to a lateral side of each blood product 23 in the form of a bag. The operator who handles the blood product 23 has an IC card which stores ID information specific to the operator.

This embodiment includes an information reading means (not shown) to read the information stored in the IC tag 79 and IC card and the specific information on the blood product 23 taken in and out and the ID information on the operator who took it in and out are recorded in the recording/display unit 28 along with the time when the information was read.

The insulating cover body 6 is opened and closed to take in and out the blood product 23 and a cover opening/closing detecting section 54 for detecting opening/closing motion of the insulating cover body 6 is provided near the joint between the insulating container 5 and the insulating cover body 6.

The cover opening/closing detecting section 54 is a contactless cover opening/closing sensor which includes an electromagnetic sensor 55 using a Hall element and a magnet 56. The electromagnetic sensor 55 is attached to the insulating container 5 and the magnet 56 is attached to the cover body 6.

The cover opening/closing detecting section 54 detects opening/closing motion of the insulating cover body 6 and records the time when the insulating cover body 6 was opened/closed and the storage temperature data at that time in the recording/display unit 28.

Consequently, opening or closing of the insulating cover body 6 is detected even at a time other than when taking in or out the blood product 23, which makes it possible to check whether temperature control of the blood product 23 has been properly done. In addition, the cover opening/closing detecting section 54 is connected to an alarm section 57 in the recording/display unit 28 and if one forgets to close the insulating cover body 6, a warning about it is given using the alarm section 57 (specifically, a buzzer, LED lamp, liquid crystal display, etc.).

Furthermore, the alarm section 57 is designed to give a warning before the internal temperature exceeds a prescribed control temperature zone. Thus, by giving a warning before the internal temperature exceeds the prescribed control temperature zone, the cause for a failure to keep the temperature (for example, a radiation fan failure, clogging of the intake/exhaust port, dust accumulation on the radiation fin, etc.) can be removed in advance so that the blood product 23 can be stored without deterioration in the quality of the blood product 23.

If the internal temperature exceeds the prescribed temperature zone, the alarm section 57 gives a warning to notify that the blood product 23 contained in the transport box is unusable.

A warning about a failure to close the insulating cover body 6, a warning before the internal temperature exceeding the prescribed control temperature zone, and a warning to notify that the internal temperature has exceeded the prescribed control temperature zone are recorded in the recording/display unit 28 along with the times when warnings were given.

In the above embodiments, an alumite-treated aluminum plate is used as a material with high thermal conductivity and high thermal radiation factor (thermal emissivity); however, instead, using a heat radiation paint (for example, a heat radiation paint based on one-liquid type thermosetting acrylic resin (Chugai Co.LTD., trade name PELCOOL)), a coating can be made on the internal heat conducting container 8 and (or) the cover internal side heat conducting plate 35 made of non-alumite-treated aluminum or on the lower surface of the casing 13 of the insulating cover body 6.

In the coating made by this paint, heat is uniformly diffused (thermally conducted) and the heat is properly radiated from the coating surface. Furthermore, the heat radiation paint is excellent in adhesiveness to metal.

Aluminum obtained by treating an aluminum compound is also used as a material which is high both in thermal conductivity and thermal radiation factor.

However, there is a problem that the third temperature zone (−20° C.) suitable for storage of frozen plasmas requires consumption of a large amount of electric power and thus frozen plasmas are not suitable for transportation based on an internal battery without an external power source. Therefore, it is necessary to take countermeasures such as limiting the use without an external power source to a very short time or increasing the thickness of the insulating layer and combining a cold storage material.

As a cold storage material, a cold storage material produced by adding an additive to lithium chloride, which can keep a constant temperature in various temperature zones, is available, so by putting a cold storage material designed to keep a temperature of −20° C. or less in the internal heat conducting container of a transport box according to the present invention, performing cold storage during the use of an external power source and using the cold storage material during transportation of frozen plasmas, the transport box can be made suitable for the temperature zone for frozen plasmas.

The temperature-regulated transport box is different from an ordinary refrigerator in the following point. The transport box is taken outdoors and the ambient temperature may largely vary with the seasons or regions and the ambient temperature may be lower than the internal temperature of the transport box. If the transport box is taken out of a room whose temperature is kept constant, to a very cold or very hot outdoor place, the ambient temperature may rapidly rise or drop.

Under such environmental conditions, the internal temperature must be kept constant. For example, for storage of red blood cells, the surface temperature of the internal container to contact the blood product must be kept within the first temperature zone of 2-6° C. In other words, in transportation of the blood product, the internal temperature including the surface temperature of the internal container must be kept within the range of 2-6° C. when the ambient temperature range is from −10° C. to 40° C.

Furthermore, in order to make it portable, it must be compact and lightweight. Also the requirement that it can run on an internal battery for many hours must be satisfied because a fixed power source is often unavailable during outdoor transportation.

Figure 19:
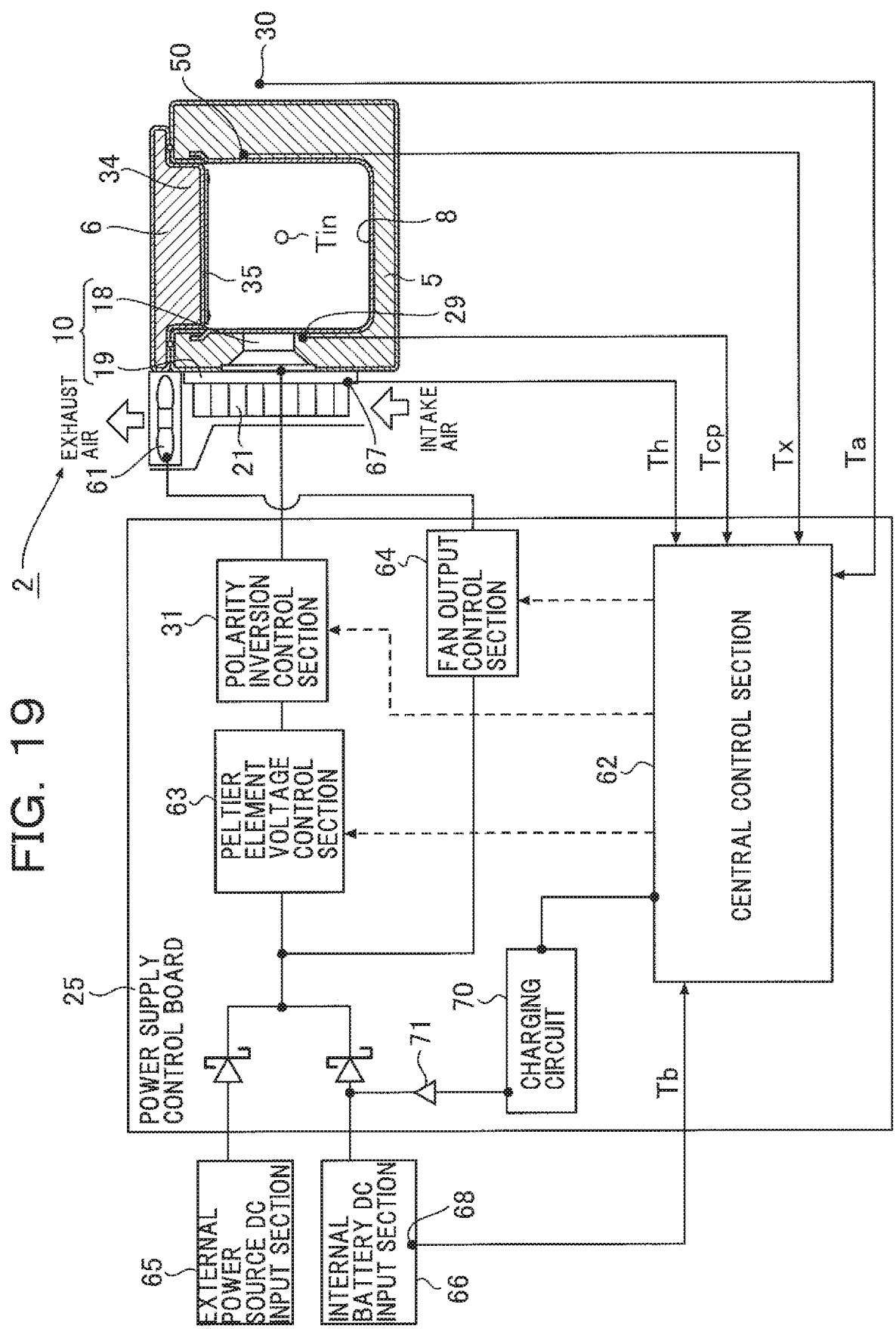
FIG. 19 is a sectional view of a transport box according to a ninth embodiment of the present invention.

FIG. 19 is a schematic block diagram of a transport box according to a ninth embodiment. As shown in FIG. 19, an axial fan 61 for cooling the radiation fin 21 of the electronic cooling unit 10 is located externally (in the housing 3).

The power supply control board 25 includes a central control section 62, Peltier element voltage control section 63, polarity inversion control section 31, and fan output control section 64. In the figure, reference sign 65 represents an external power source DC input section, 66 an internal battery DC input section, 67 an external heat exchanger temperature sensor mounted on the heat radiation side thermal conductor 19 of the electronic cooling unit 10, and 68 an internal battery temperature sensor mounted near the internal battery DC input section 66. These components are connected as shown in the figure.

Since the ambient temperature sensor 30 is located near an external air inlet in the component housing 3 which allows an air flow, accurate temperature measurement can be made without being influenced by a slight change in the external air temperature and without being influenced by internal cold or heat.

As shown in FIG. 19, power supply control temperature Tcp from the power supply control temperature sensor 29, ambient temperature Ta from the ambient temperature sensor 30, internal equivalent temperature Tx close to the internal center temperature of the internal heat conducting container 8 from the internal temperature display temperature sensor 50, external heat exchanger temperature Th from the external heat exchanger temperature sensor 67 mounted on the heat radiation side thermal conductor 19 (heat exchanger), and internal battery temperature Tb from the internal battery temperature sensor 68 are sent to the central control section 62. In the figure, Tin represents the internal center temperature.

In a transport box according to the present invention, heat conduction of the internal heat conducting container 8 itself and internal air convection on the surface of the internal heat conducting container 8 are used as main thermal homogenization means, so the internal temperature can be controlled by detecting the temperature of the internal heat conducting container 8. Also, the transport box must provide a function to measure the internal temperature and display and record it.

However, it is difficult to control power output to the electronic cooling unit 10 on the basis of internal equivalent temperature Tx from the internal temperature display temperature sensor 50 to keep the internal temperature constant.

Figure 20:
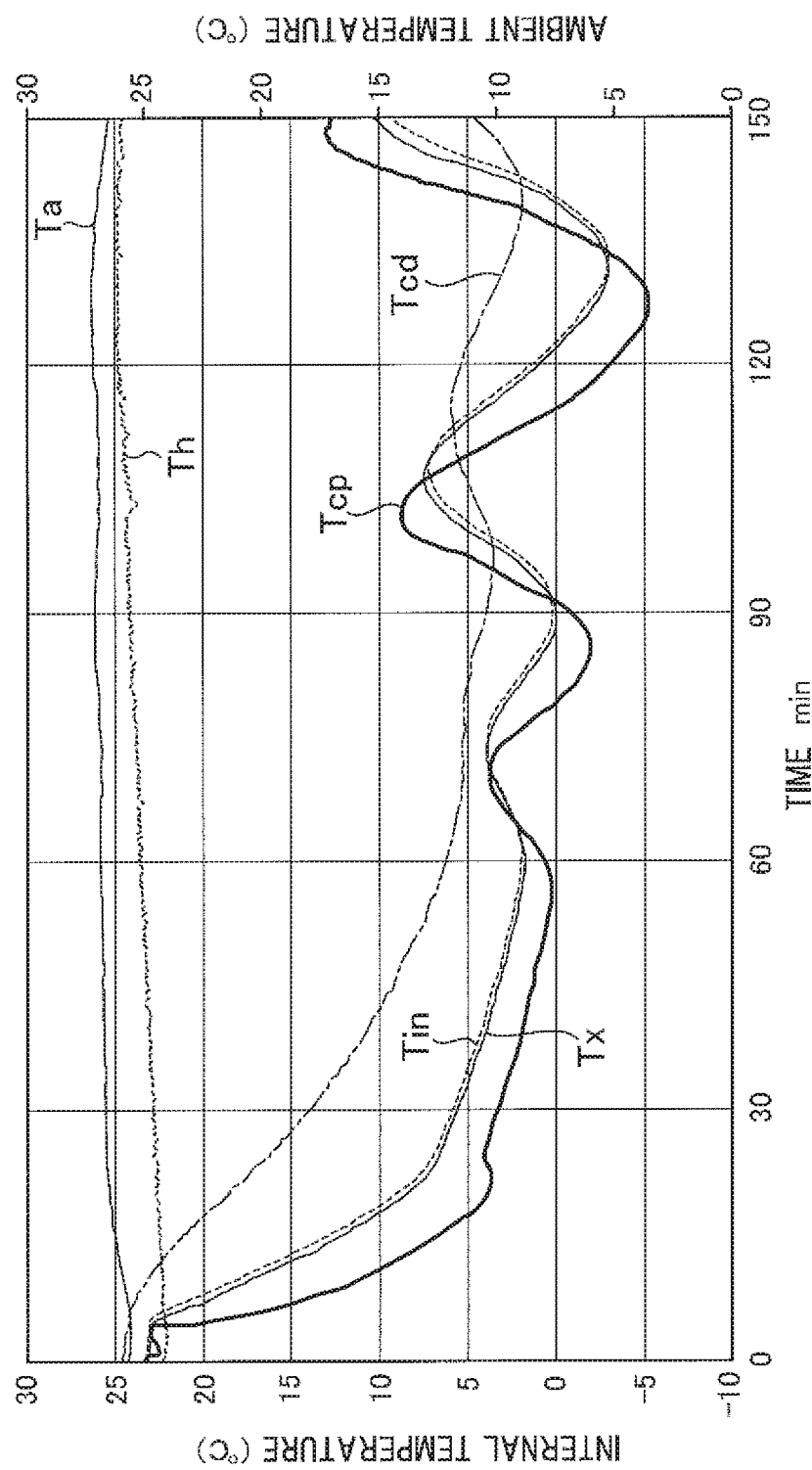
FIG. 20 is a temperature characteristic graph which explains inconvenience controlling power output to the electronic cooling unit on the basis of internal equivalent temperature Tx.

FIG. 20 is a temperature characteristic graph which explains it. FIG. 20 shows ambient temperature Ta, external heat exchanger temperature Th, power supply control temperature Tcp, internal center temperature Tin, internal equivalent temperature Tx, and bottom temperature Tcd of the internal heat conducting container 8 when power output to the electronic cooling unit 10 is controlled on the basis the internal equivalent temperature Tx detected by the internal temperature display temperature sensor 50 under the condition of ambient temperature Ta of 25° C.

As apparent from this figure, the temperatures at various spots (Tcp, Tin, Tx, Tcd) change and are hard to stabilize. This is because even if internal thermal uniformity is enhanced for the main internal portion (in this embodiment, the side surface opposite to the side surface where the power supply control temperature sensor 29 of the internal heat conducting container 8 is mounted), heat conduction to an area remote from the electronic cooling unit 10 takes time and thus when control is done on the basis of the temperature of the remote area from the electronic cooling unit 10, variation in the temperature near the electronic cooling unit 10 is large.

Figure 21:
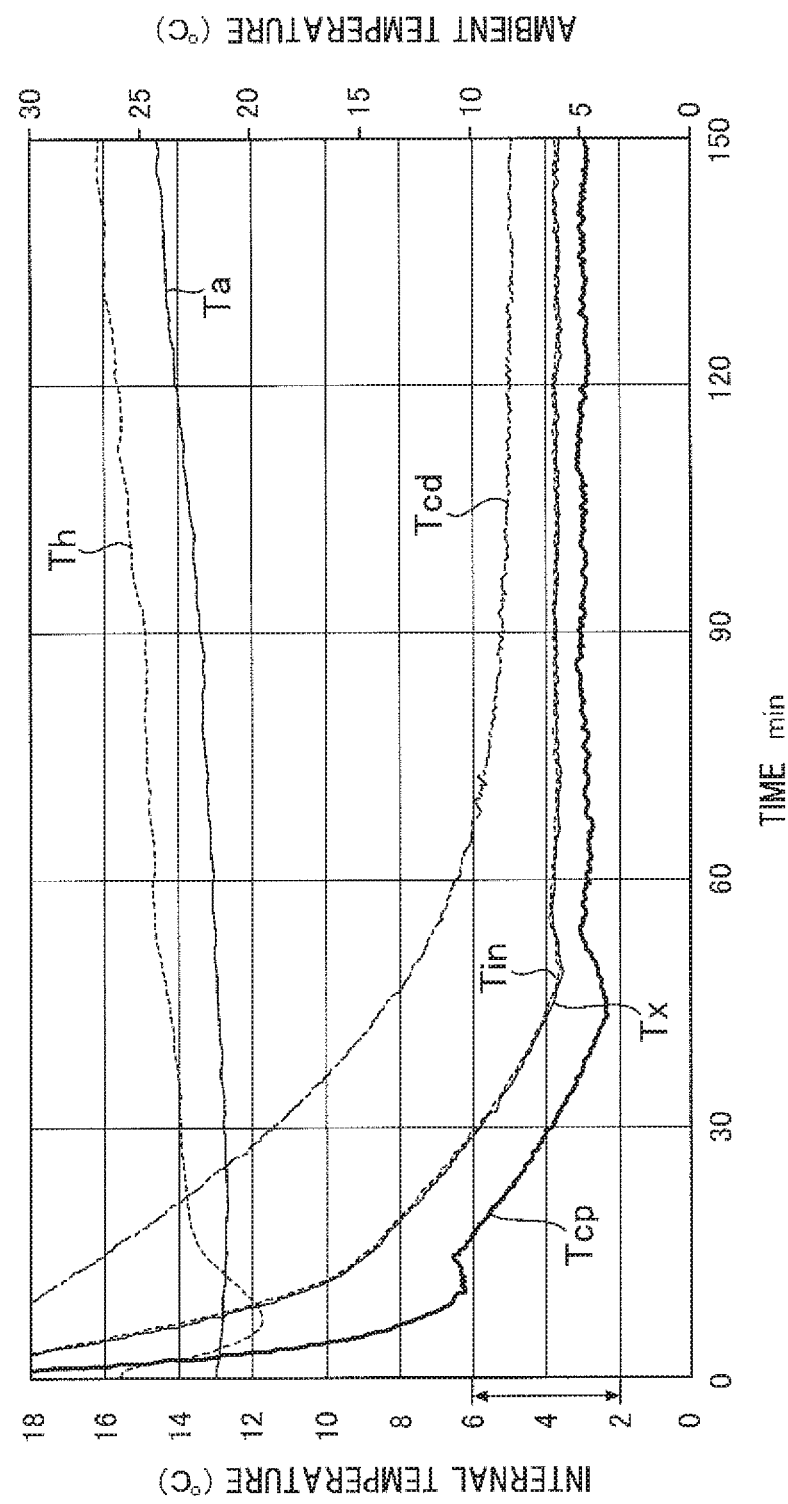
FIG. 21 is an internal temperature characteristic graph in which power output to the electronic cooling unit is controlled on the basis of power supply control temperature Tcp and the power output is corrected by the detected ambient temperature Ta.

FIG. 21 is a temperature characteristic graph in which the power supply control temperature sensor 29 is mounted on the side surface of the internal heat conducting container 8 in contact with the heat absorption side thermal conductor 18 of the electronic cooling unit 10 and power output to the electronic cooling unit 10 is controlled on the basis of power supply control temperature Tcp detected by it and the power output is corrected by the detected ambient temperature Ta.

In other words, the value of current supplied to the Peltier element 20 is adjusted according to the ambient temperature so that a detection signal from the ambient temperature sensor 30 is sent to the power supply control board 25 and the internal temperature is stabilized at the preset temperate.

As apparent from FIG. 21, by controlling power output to the electronic cooling unit 10 on the basis of power supply control temperature Tcp from the power supply control temperature sensor 29, internal temperature variation as shown in FIG. 20 does not occur and first the power supply control temperature Tcp enters the first temperature zone (2-6° C.) as a temperature target, then the internal center temperature Tin, internal equivalent temperature Tx, and bottom temperature Tcd of the internal heat conducting container 8 are also controlled within the control temperature zone so that control is performed stably.

When the ambient temperature Ta is stable, the power supply control temperature Tcp to control the internal temperature to a constant level is constant and it is only necessary to control the amount of power supply to the electronic cooling unit 10 so as to keep the temperature. Therefore, if variation in the ambient temperature Ta is small, control can be performed stably by correction using the ambient temperature Ta on the basis of the power supply control temperature Tcp.

However, if the ambient temperature Ta varies largely, the internal temperature is affected by the ambient temperature Ta and if the ambient temperature Ta is high, the internal temperature also becomes high and if the ambient temperature Ta is low, the internal temperature also becomes low. Therefore, if the target power supply control temperature Tcp for control of the internal temperature remains constant, the internal temperature Ta would change according to the ambient temperature Ta.

Figure 22:
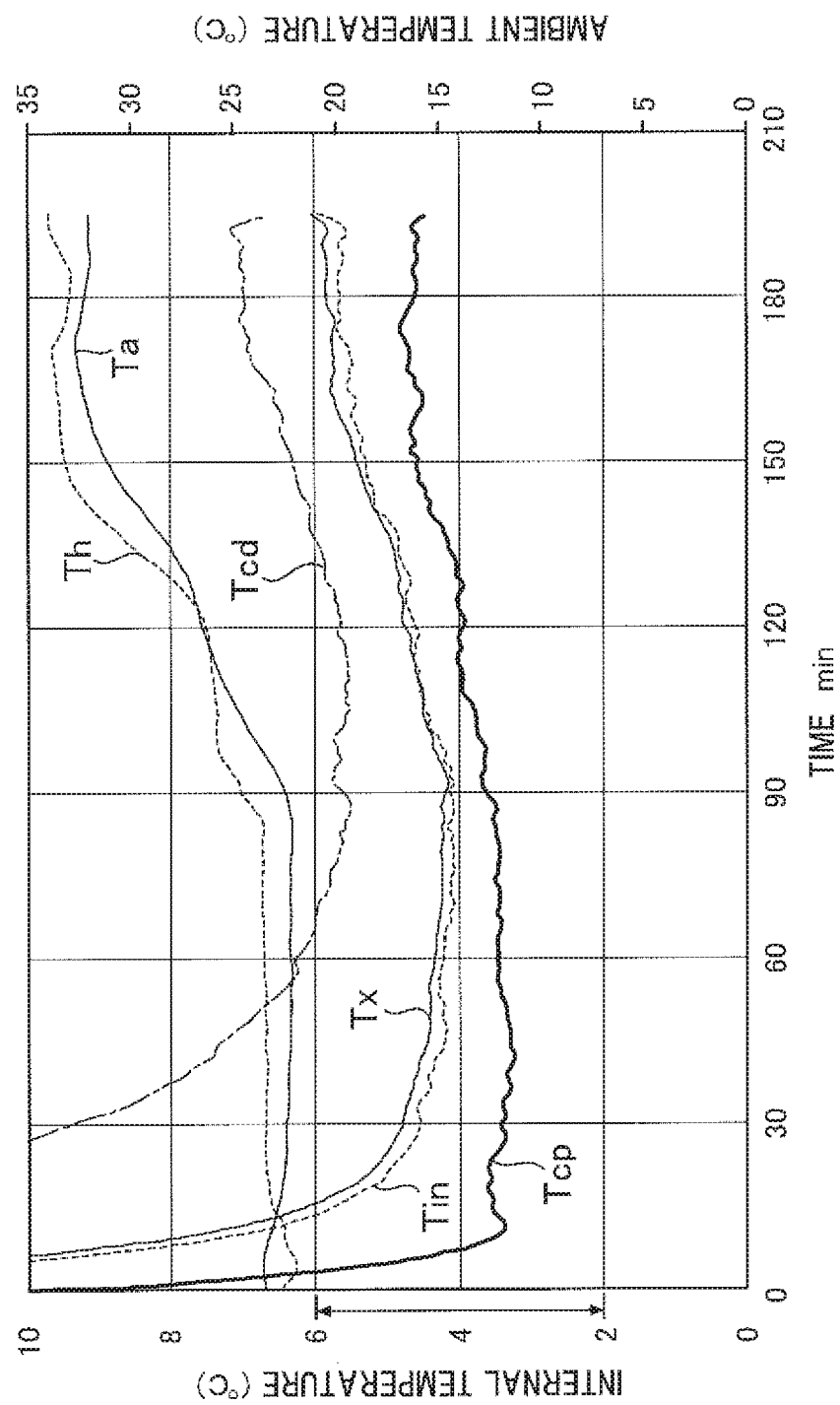
FIG. 22 is an internal temperature characteristic graph showing internal temperatures with gradual increase in the ambient temperature Ta when the target power supply control temperature Tcp is unchanged.

FIG. 22 is a temperature characteristic graph showing changes in the internal temperatures (Tcp, Tin, Tx, Tcd) with gradual increase in the ambient temperature Ta when control is done with the target power supply control temperature Tcp unchanged (fixed) under the condition of an ambient temperature of 25° C.

As can be known from the figure, when the ambient temperature Ta increases, accordingly the actual power supply control temperature Tcp, internal center temperature Tin, internal equivalent temperature Tx, and bottom temperature Tcd of the internal heat conducting container 8 also increase gradually with the elapse of time and when the ambient temperature Ta exceeds 30° C., the internal temperatures exceed the upper limit of the first temperature zone of 6° C.

Therefore, the target power supply control temperature Tcp at an ambient temperature Ta of 25° C. (reference) is set as a reference value and various experiments are carried out to correct the target power supply control temperature Tcp with variation in the ambient temperature Ta and the relation between different ambient temperatures Ta and corrected target power supply control temperatures Tcp' is tabularized and stored in the central control section 62 (see FIG. 19).

Figure 23:
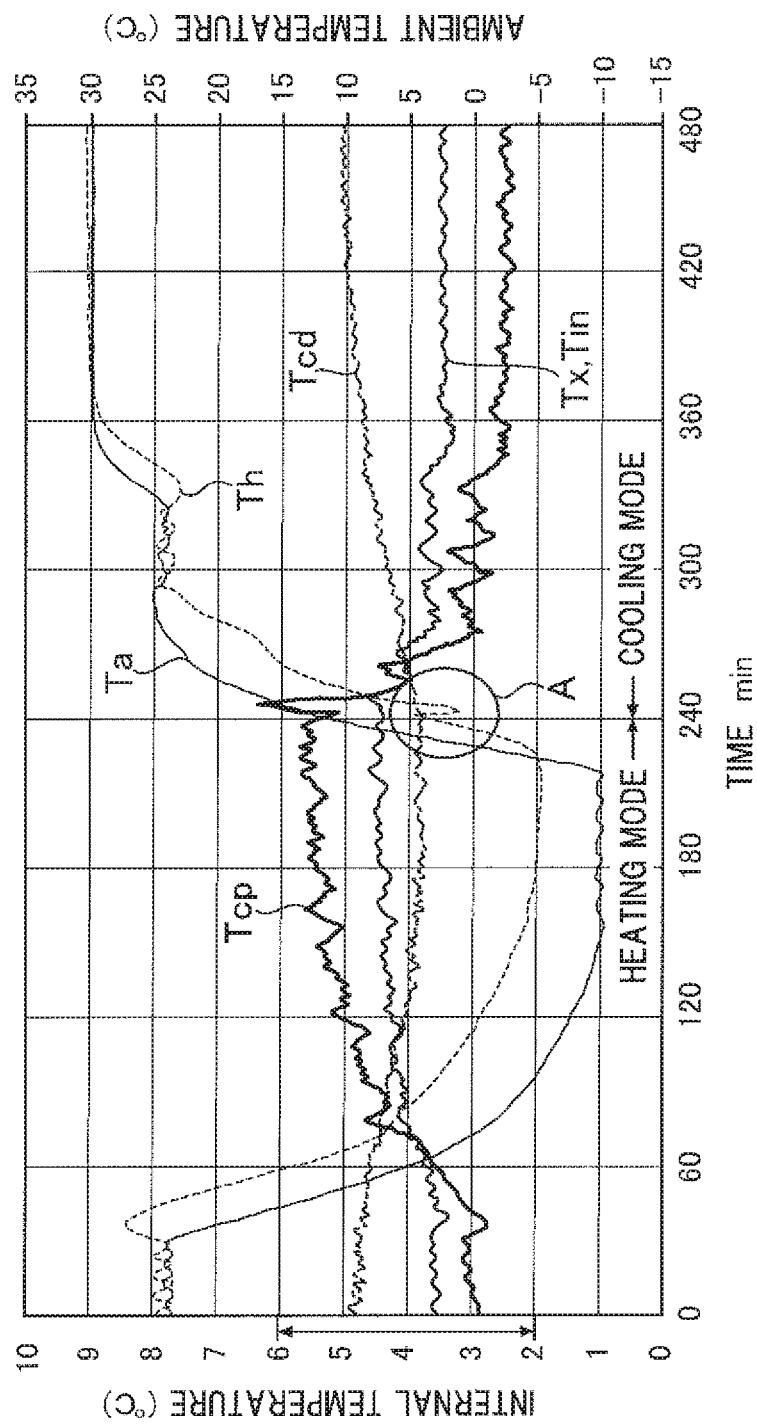
FIG. 23 is a temperature characteristic graph in which rotation of the fan is resumed at the time of return from the heating mode to the cooling mode.

FIG. 23 is a temperature characteristic graph showing changes in the internal temperatures and ambient temperature, in which the ambient temperature is lower than the internal temperatures and the polarity of voltage applied to the electronic cooling unit 10 is inverted by the polarity inversion control section 31 (see FIG. 19) to use the heating mode.

In the figure, Th represents an external heat exchanger temperature. In this test, when the electronic cooling unit 10 is used in the heating mode, the fan 61 (see FIG. 19) is stopped for the purpose of power saving and when the mode is returned from the heating mode to the cooling mode, the external heat exchanger temperature Th may change discontinuously as indicated by area A of FIG. 23. Due to this, the internal temperatures (Tcp, Tin, Tx, Tcd) also change largely.

This indicates that the internal temperatures (Tcp, Tin, Tx, Tcd) are controlled in the heating mode while the fan 61 is stopped and when the electronic cooling unit 10 returns from the heating mode to the cooling mode, the fan 61 is restarted, which causes variation in the external heat exchanger temperature Th in area A, resulting in an imbalance in internal temperature control.

Figure 24:
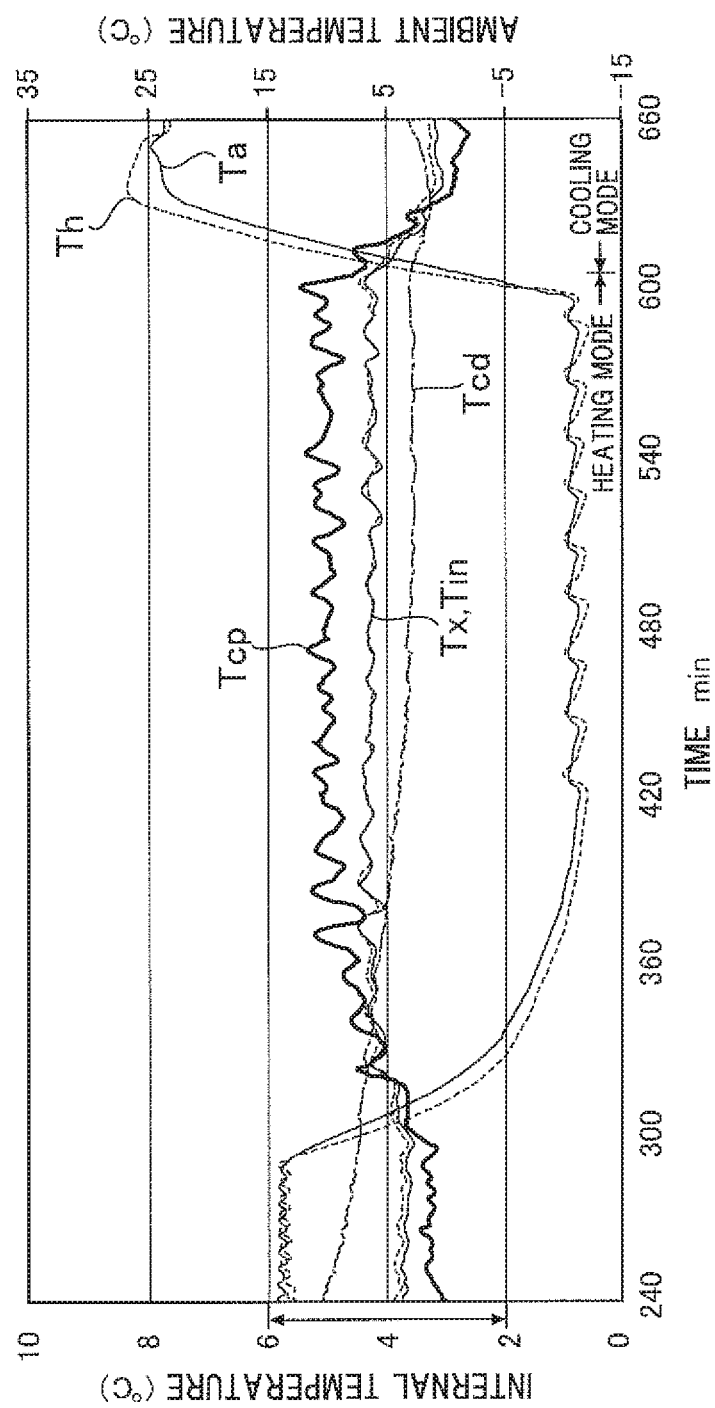
FIG. 24 is a temperature characteristic graph in which rotation of the fan is continued whether in the heating mode or cooling mode.

FIG. 24 is a characteristic graph showing changes in the internal temperatures and ambient temperature in which the ambient temperature is lower than the internal temperatures and the polarity of voltage applied to the electronic cooling unit 10 is inverted as in FIG. 23 and the heating mode is used.

In this test, the external fan 61 (see FIG. 19) continuously rotates even when the mode is switched to the heating mode, so the internal temperatures (Tcp, Tin, Tx, Tcd) are more stable within the prescribed temperature range than in the case of FIG. 23.

Figure 25:
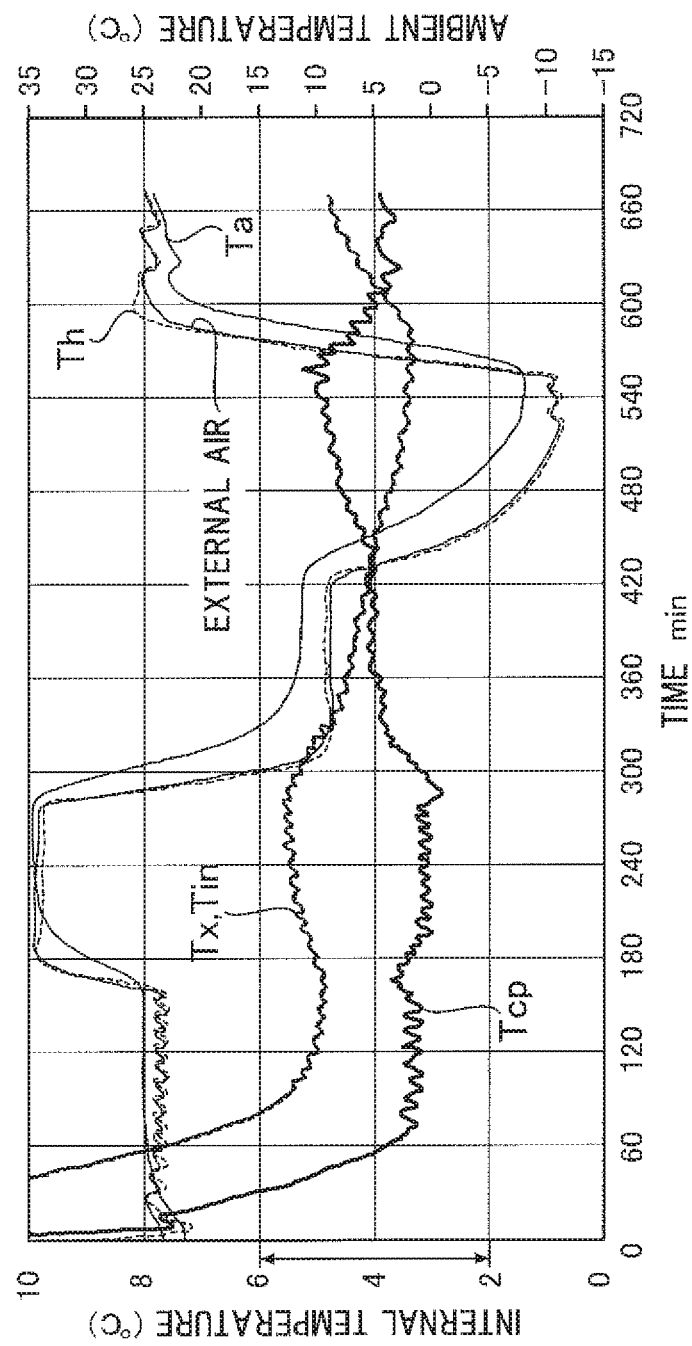
FIG. 25 is a temperature characteristic graph showing changes in the internal temperatures and ambient temperature when the ambient temperature changes largely.

FIG. 25 is a temperature characteristic graph showing changes in the internal temperatures and ambient temperature when the actual ambient temperature (indicated as external air) changes largely.

In the figure, Ta represents an ambient temperature detected by the ambient temperature sensor 30. As in this test, when rapid change from an actual ambient temperature of 35° C. to a room temperature of 20° C. or from an ambient temperature of −10° C. to a room temperature of 25° C. occurs, the ambient temperature sensor 30 follows the change with a delay in response. This is because, in order to prevent the ambient temperature sensor 30 from changing largely in response to a slight change in the actual ambient temperature, the ambient temperature sensor 30 is mounted in the housing 3 which is somewhat slow in response to the ambient temperature, so that its sensitivity is slightly decreased.

Consequently the internal temperatures change without immediately responding to a rapid temperature change. In this test, the internal temperatures do not exceed the prescribed temperature range, but they may be out of the range under some condition.

On the other hand, the external heat exchanger temperature sensor 67 for detecting external heat exchanger temperature Th is highly responsive to change in the actual ambient temperature partly because it is installed on the air suction side as shown in FIG. 19. Therefore, it is effective as a temperature sensor which detects the point of change when a rapid temperature change occurs.

Therefore, when the actual ambient temperature changes largely, internal temperature control is done more stably by adding control by correction using the external heat exchanger temperature Th for decision about sudden change of external air on the basis of power supply control temperature Tcp than by correction using the ambient temperature Ta on the basis of power supply control temperature Tcp.

In addition, by monitoring the external heat exchanger temperature Th constantly, malfunctioning of the heat radiation side heat exchanger system, such as a failure of the fan 61, clogging of the intake/exhaust pipe, or radiation performance decline due to dust accumulation on the radiation fin 21, can be detected before it becomes impossible to keep the internal temperature, and the operator can be notified by the alarm section 57 (see FIG. 18). Furthermore, the running condition of the fan 61 can be monitored by measurement of the external heat exchanger temperature Th.

Figure 26:
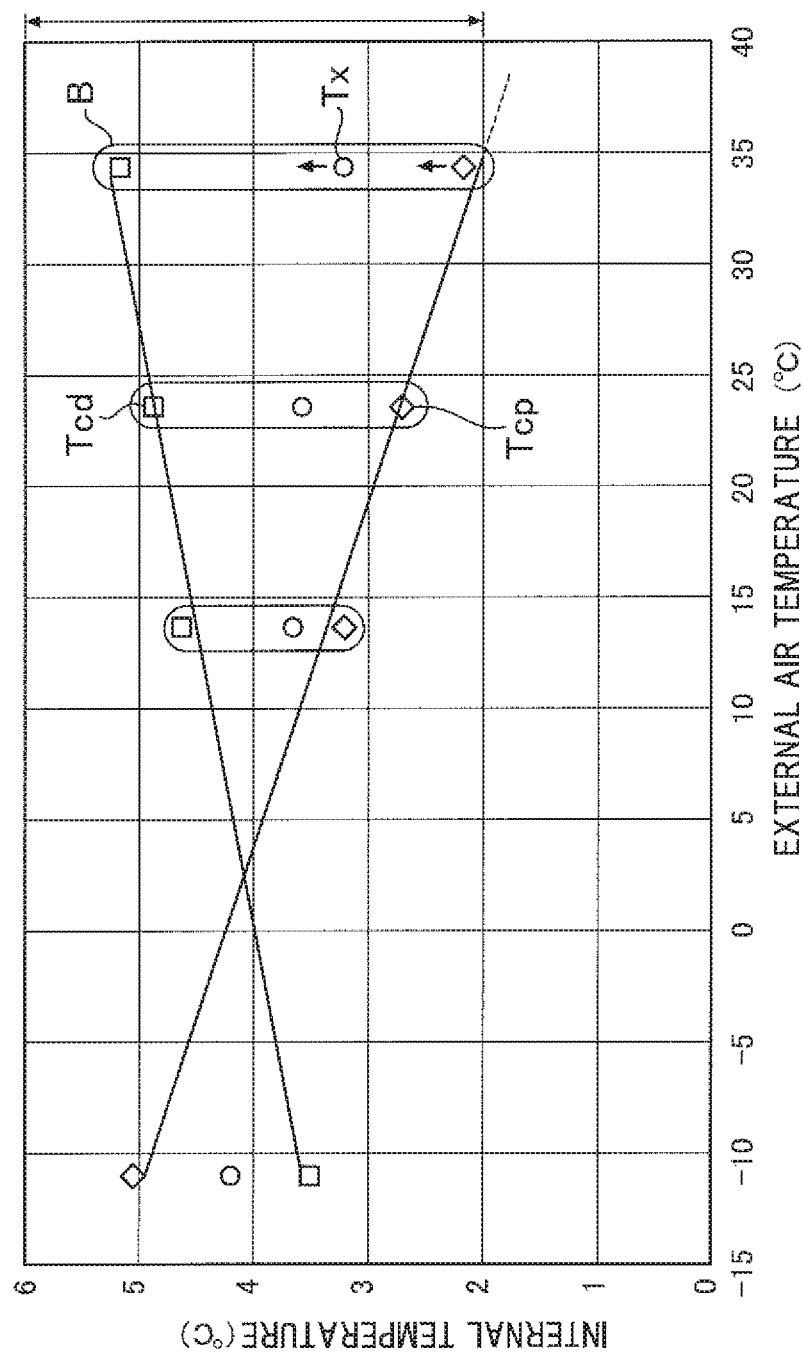
FIG. 26 is a graph showing changes in internal temperatures (Tcp, Tx, Tcd) and internal temperature distributions with change in the ambient temperature.

The internal temperatures (Tcp, Tx, Tcd) and internal temperature distribution change as the ambient temperature changes. FIG. 26 shows the tendency of such change. As shown in FIG. 26, when the ambient temperature is 35° C., the internal temperatures (Tcp, Tx, Tcd) and internal temperature distribution (encircled by oblong circles) are within the prescribed temperature range (2-6° C. in this embodiment).

However, at this time the power supply control temperature Tcp is nearly 2° C., so if the ambient temperature becomes higher than this, the temperature distribution (power supply temperature Tcp) will be out of the prescribed temperature range as indicated by dotted line.

At this time, the internal equivalent temperature Tx is close to the internal center temperature or nearly 3° C. Thus, when the ambient temperature sensor 30 detects that the ambient temperature Ta is 35° C. or more, the internal equivalent temperature Tx is shifted upward as indicated by an arrow (for example, from 3° C. to 4° C. to control the internal equivalent temperature Tx to 4° C.), and accordingly the power supply control temperature Tcp is also shifted upward averagely so that the temperature distribution is within the prescribed temperature range. When in relation to the ambient temperature Ta the internal equivalent temperature Tx deviates from the target temperature, control by correction of the difference between the set internal temperature Tin and internal equivalent temperature Tx is effective in controlling the internal temperature distribution within the target temperature zone when the external air temperature zone is wide.

In winter, when the transport box is taken outdoors at 0° C. or less and used for transportation, the temperature of the housing 3 is often below 0° C. From the test conducted by the present inventor, it has been confirmed that when the ambient temperature Ta was −11° C., the temperature of the housing 3 was nearly −10° C.

On the other hand, the lithium ion battery (internal battery 26) built in the transport box is small and lightweight and can store high density electrical energy, so it is an ideal battery for transportation. However, charging of the lithium ion battery below 0° C. is dangerous and charging must be stopped below 0° C. Also, when the external air temperature (ambient temperature) is 40° C. or more, charging of the lithium ion battery is dangerous and must be stopped.

For this reason, in this embodiment, as shown in FIG. 19, an internal battery temperature sensor 68 is attached near the internal battery 26 (lithium ion battery) or directly to the internal battery 26. The detected internal battery temperature is sent to the central control section 62.

The power supply control board 25 also includes a charging circuit 70 and a charge stopping means 71 to stop charging of the internal battery 26. As the internal battery temperature becomes close to 0° C. (for example, 5° C. or less) or the external temperature (ambient temperature) becomes 40° C. or more, charging of the internal battery 26 is automatically stopped according to a decision made by the power supply control board 25.

A possible method for management of the blood product 23 may be that an RFID tag (IC tag) is attached to the blood product 23 so that the operator holds the blood product 23 by hand and brings the RFID tag (IC tag) near to an RFID antenna (high frequency antenna) attached to the transport box so as to read information for management.

However, regarding management in connection with taking the blood product 23 into and out of the transport box, it must be taken into account that the transport box is handled by many unspecified operators. Therefore, a management system which automatically detects and records the blood product 23 to be taken in and out without data reading work by an operator is needed.

Meanwhile, simply by reading the RFID tag on the blood product 23 taken into or out of the transport box with the insulating cover body 6 open, whether it has been put in the transport box or has been taken out of the transport box cannot be determined, so eventually the RFID tag in the box must be read with the insulating cover body 6 closed.

Figure 27:
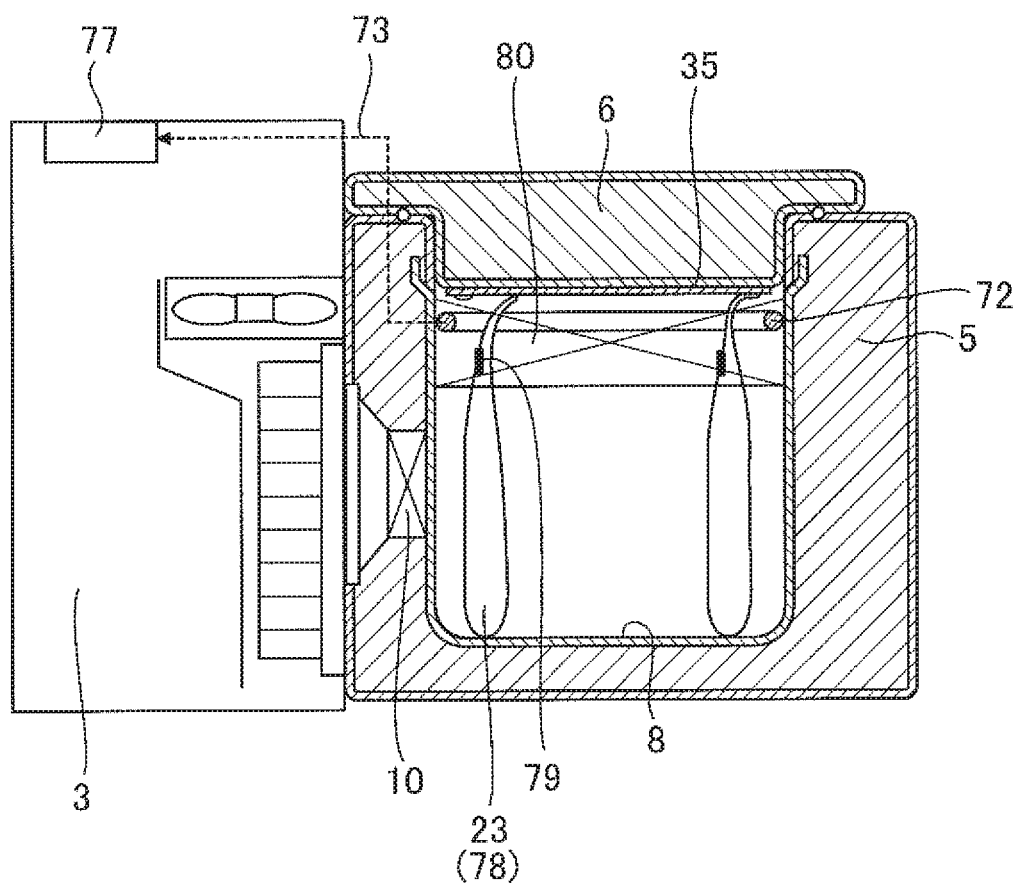
FIG. 27 is a fragmentary sectional view of a transport box according to a tenth embodiment of the present invention.
Figure 28:
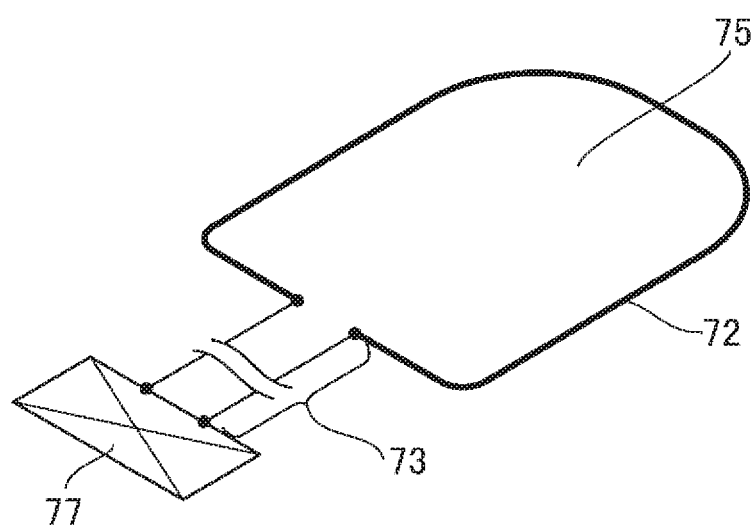
FIG. 28 is a schematic view of information reading means used for the transport box.

FIG. 27 is a fragmentary sectional view of a transport box according to a tenth embodiment and FIG. 28 is a schematic view of information reading means.

In this embodiment, as shown in FIG. 27, a loop antenna 72 is mounted on the inside of the opening end of the internal heat conducting container 8. As shown in FIG. 28, both ends of the antenna 72 are connected to an RFID reader/writer 77 through an antenna lead wire 73. A space area 75 through which the blood product 23 can pass freely is formed inside the antenna 72.

The RFID reader/writer 77 is installed in the housing 3 and connected to the operation panel (not shown) over the housing 3. The antenna 72, antenna lead wire 73 and RFID reader/writer 77 constitute information reading means.

Also, an RFID tag 79 storing many types of information on the blood product 23 is attached to an upper portion of a bag 78 containing the blood product 23 as shown in FIG. 27.

The antenna 72 in the transport box must be located so as to ensure that the RFID tag 79 on the contained blood product 23 can be read and the position of the antenna 72 and the position of the RFID tag 79 must be regulated to some extent. In FIG. 27, reference sign 80 represents the area of detection by the antenna 72, and the position of the antenna 72 is determined so that the RFID tags 79 of all the contained blood products 23 are always within the detection area 80.

When the insulating cover body 6 is opened and the blood product 23 is taken out or in through the opening part 7 of the insulating container 5, the RFID tag 79 is not read. When taking-out or taking-in of the blood product 23 is finished and the insulating cover body 6 is closed, the RFID tags 79 of all the blood products 23 in the box are automatically read and the read information is recorded and displayed.

Therefore, there is no need for the operator to read information when taking them in or out; as the operator takes in or out the blood products 23, the RFID tags 79 of the blood products 23 present in the transport box at that time are read and consequently, management of the individual blood products 23 taken in and out is done easily and reliably.

Figure 29:
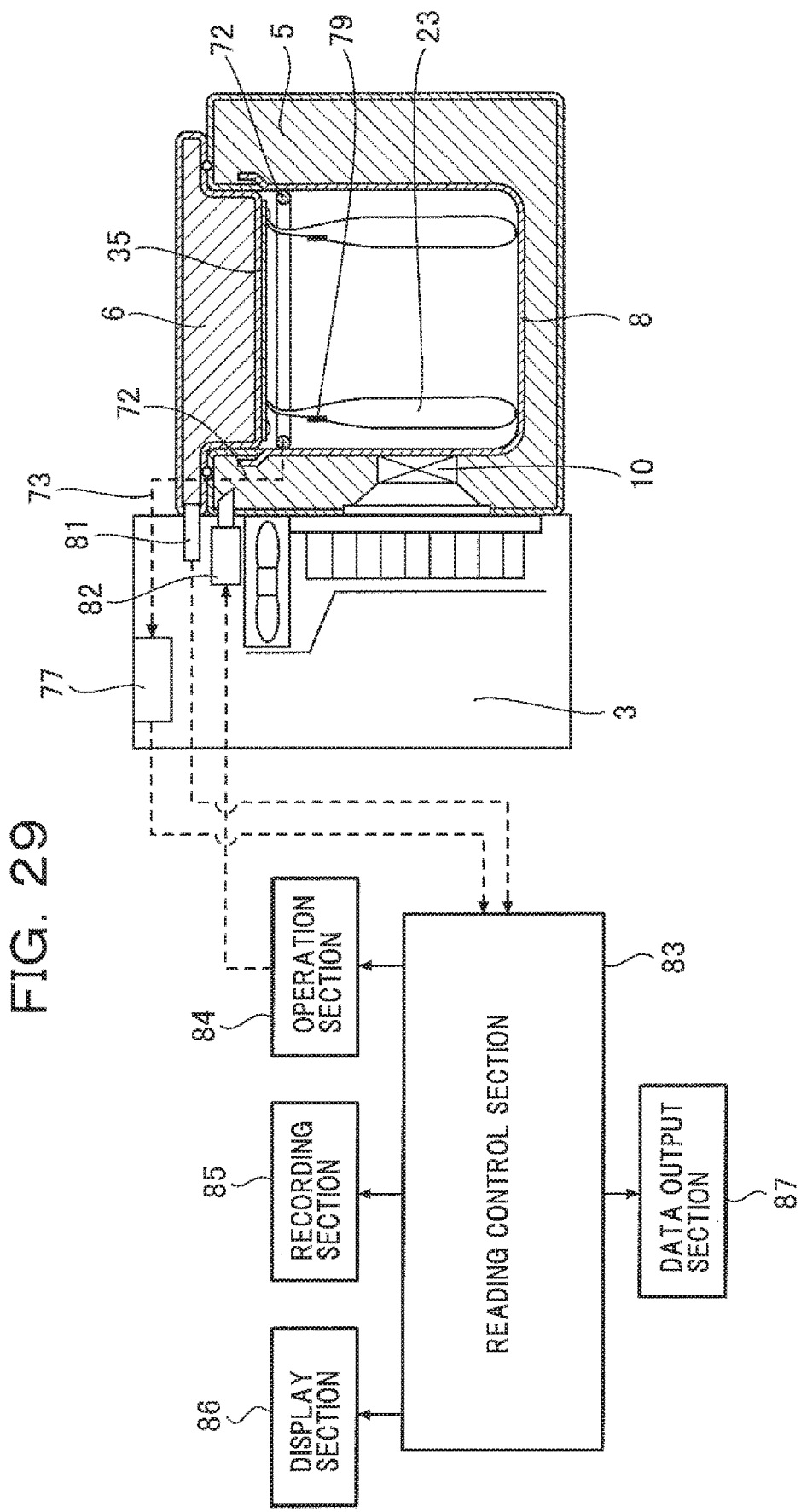
FIG. 29 a schematic view illustrating a tag reading control system in the transport box.

FIG. 29 is a schematic view illustrating the reading control system of the RFID tag 79. As shown in the figure, a cover opening/closing sensor 81 for detecting opening/closing motion of the insulating cover body 6 and cover lock means 82 for preventing an accidental opening of the insulating cover body 6 are provided between the housing 3 and the insulating cover body 6.

In this embodiment, the cover opening/closing sensor 81 includes a permanent magnet and a magnetic sensor for detecting the approach of the permanent magnet. The cover lock means 82 includes an electromagnetic solenoid and an engaging part for engaging and disengaging the electromagnetic solenoid by taking its plunger in and out.

The antenna 72 is connected to the RFID reader/writer 77 by the lead wire 73 and the information read by the RFID reader/writer 77 through the antenna 72 is sent to the reading control section 83.

Information on cover opening/closing is sent to the reading control section 83 by the cover opening/closing sensor 81. Furthermore, the reading control section 83 gives a cover lock instruction to the cover lock means 82 through an operation section 84 according to cover closing information and the insulating cover body 6 is locked.

The reading control section 83 sends necessary information to a recording section 85, display section 86 and data output section 87.

How this reading control system for the RFID tag 79 works to take in and out the blood product 23 will be explained below.

When the transport box is not used, the insulating cover body 6 is closed and locked by the cover lock means 82 and according to an instruction from the operation section 84 the cover lock means 82 is unlocked and the insulating cover body 6 is opened to take in a given blood product 23.

As taking-in of the blood product 23 is finished and the insulating cover body 6 is closed, the closing motion is detected by the cover opening/closing sensor 81 and according to the detection signal, the closed state of the insulating cover body 6 is locked by the cover lock means 82 and the blood product 23 in this state is transported.

Furthermore, the closing motion of the insulating cover body 6 is detected by the cover opening/closing sensor 81 and the information on the RFID tag 79 attached to the blood product 23 in the transport box is read by the antenna 72 and it is recorded in the recording section 85 so that information on all the blood products 23 being transported can be understood.

As the blood product 23 is transported to a specified place, the insulating cover body 6 is unlocked and opened and the required blood product 23 is taken out of the insulating container 5. At the time when the blood product 23 is taken out and the insulating cover body 6 is closed, the RFID tag 79 in the box is read by the antenna 72 and the RFID tag 79 taken out is recorded and the RFID tags 79 in the box are checked and recorded.

In this embodiment, the loop antenna 72 is used; however, instead, a board type RFID antenna may be mounted on each of the four sides of the opening part 17 of the insulating container 5 to read the information on the RFID tag 79.

However, if the length of one side of the opening part 17 of the insulating container 5 is 130 mm or so, the loop antenna 72 is more preferable because the RFID antenna using an FPC board is low in machining flexibility.

Figure 30:
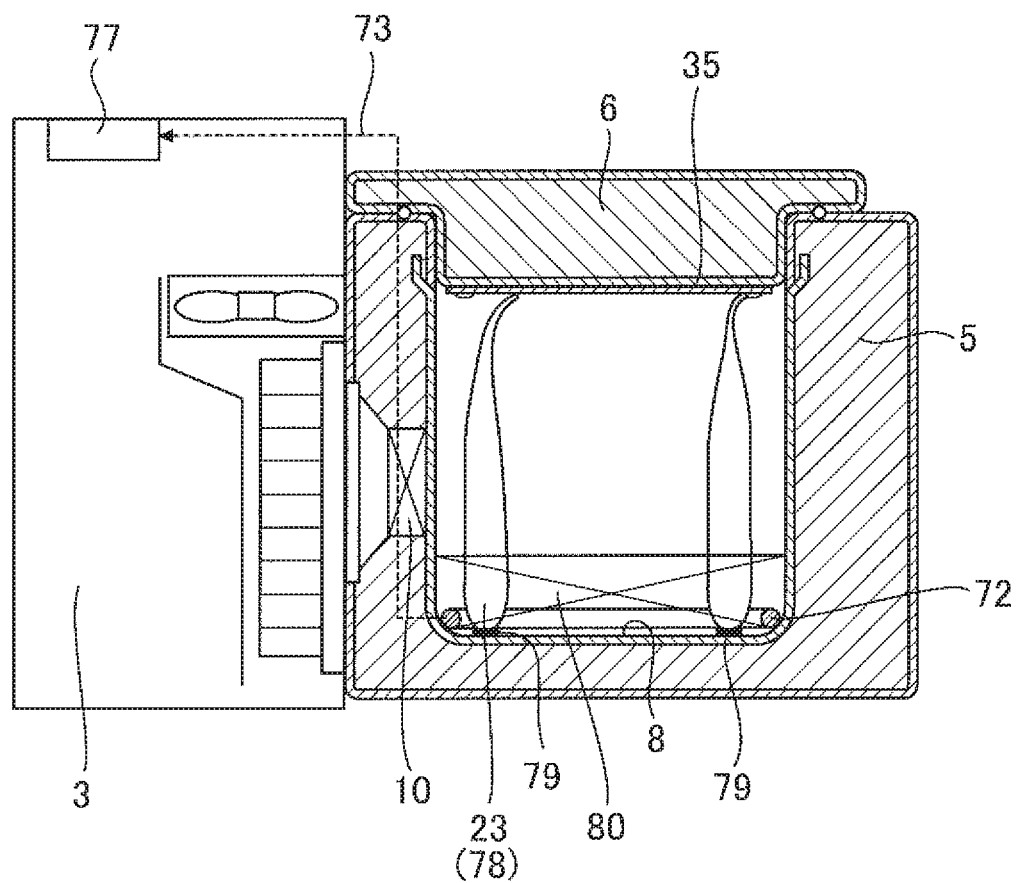
FIG. 30 is a fragmentary sectional view of a transport box according to an eleventh embodiment of the present invention.

FIG. 30 is a fragmentary sectional view of a transport box according to an eleventh embodiment. The difference of this embodiment from the tenth embodiment is that an antenna 72 is mounted on the bottom inside of the internal heat conducting container 8 and accordingly an RFID tag 79 is attached to a lower portion of the blood product 23, for example, its bottom.

In the present invention, in order to improve the information reading accuracy by regulating the position and posture of the blood product 23 (RFID tag 79) in the transport box, it is desirable to use partitioning members 47 (see FIG. 15) or rack 51 (see FIG. 16) to hold the blood products 23 in an upright position separately.

A UHF antenna is not suitable for a compact lightweight transport box since it may read the RFID tag 79 of the blood product 23 outside the transport box when the insulating cover body 6 is opened and also it is structurally large. Also, an HF band antenna formed on a board is not suitable for a compact transport box in terms of shape and cost since it is relatively large in size and has a curved corner.

In this respect, the transport boxes according to the tenth and eleventh embodiments can make the most of the housing space and allow the RFID tag 79 to be read stably.

Figure 31:
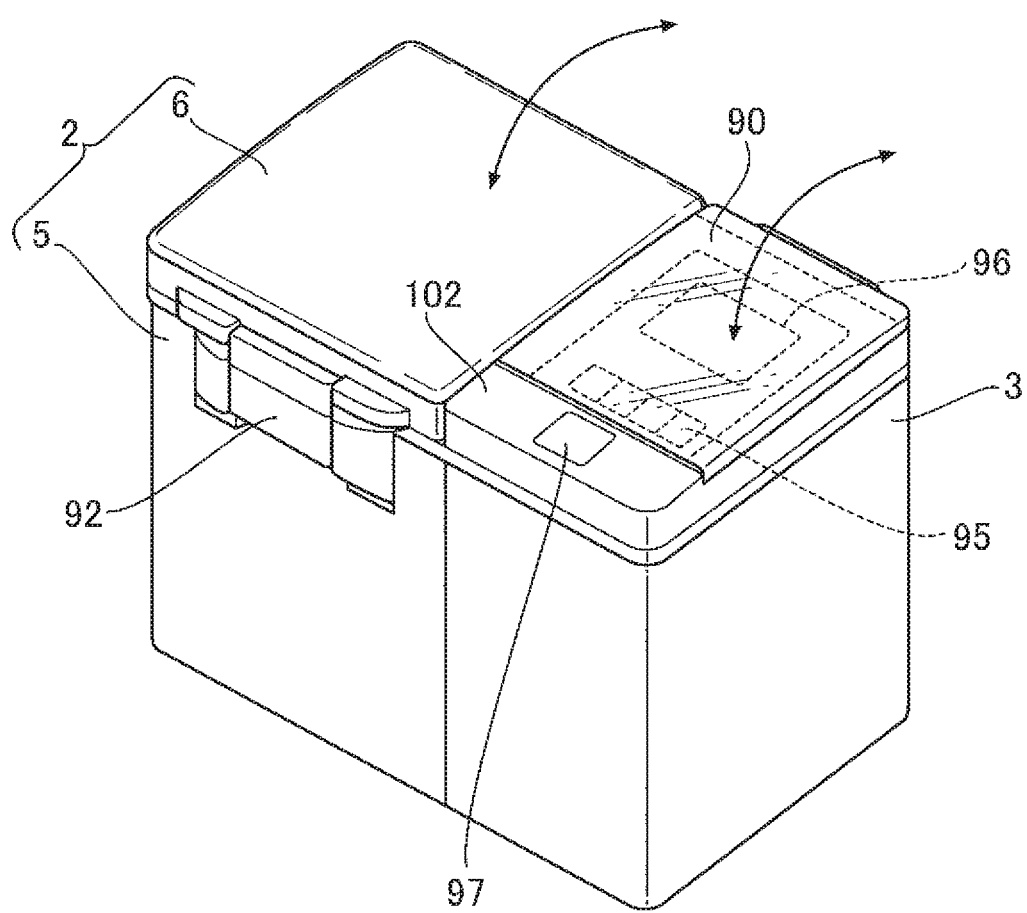
FIG. 31 is a diagrammatic perspective view of a transport box according to a twelfth embodiment of the present invention.
Figure 32:
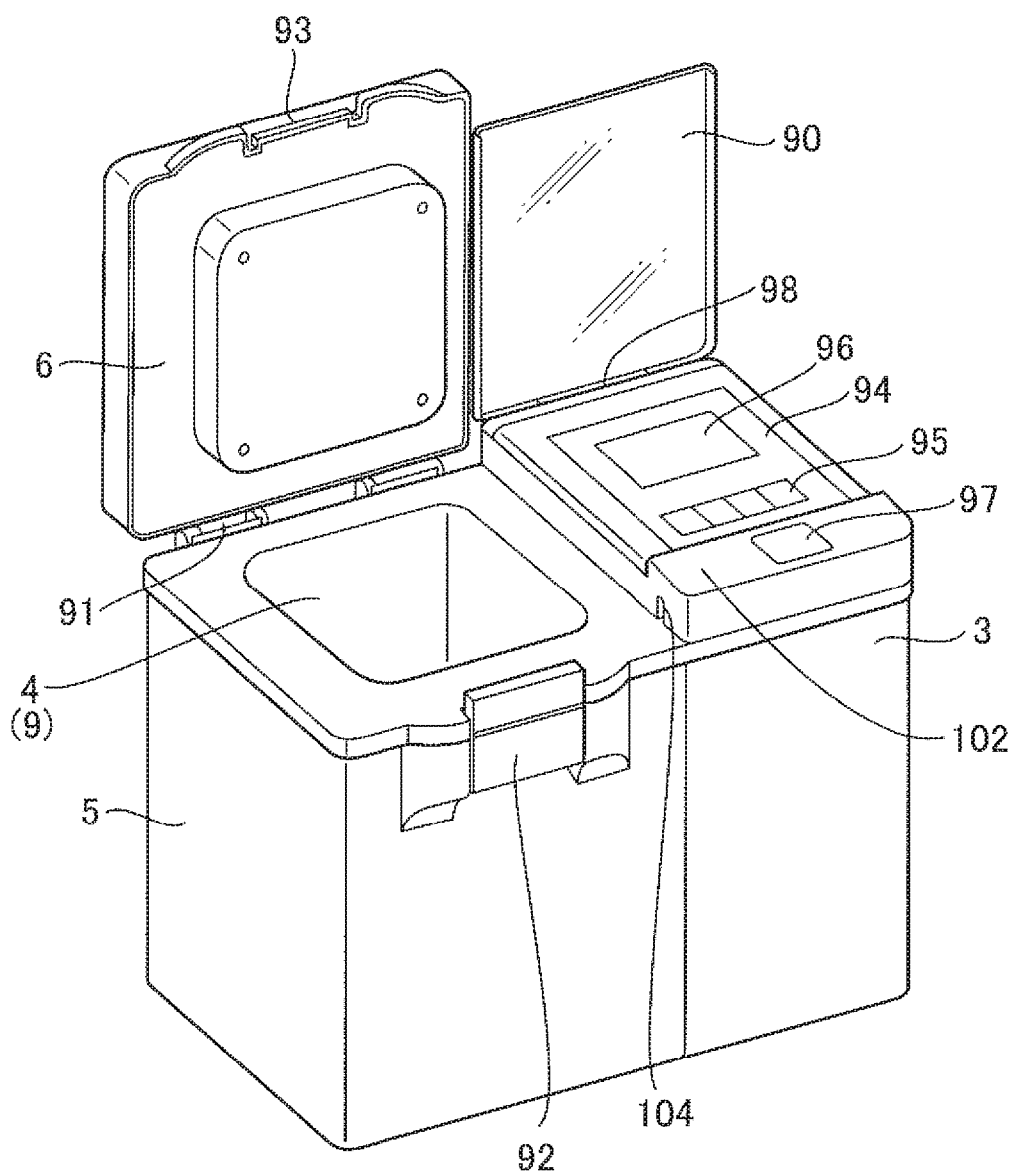
FIG. 32 is a diagrammatic perspective view of the transport box with both an insulating cover body and a protective plate open.
Figure 33:
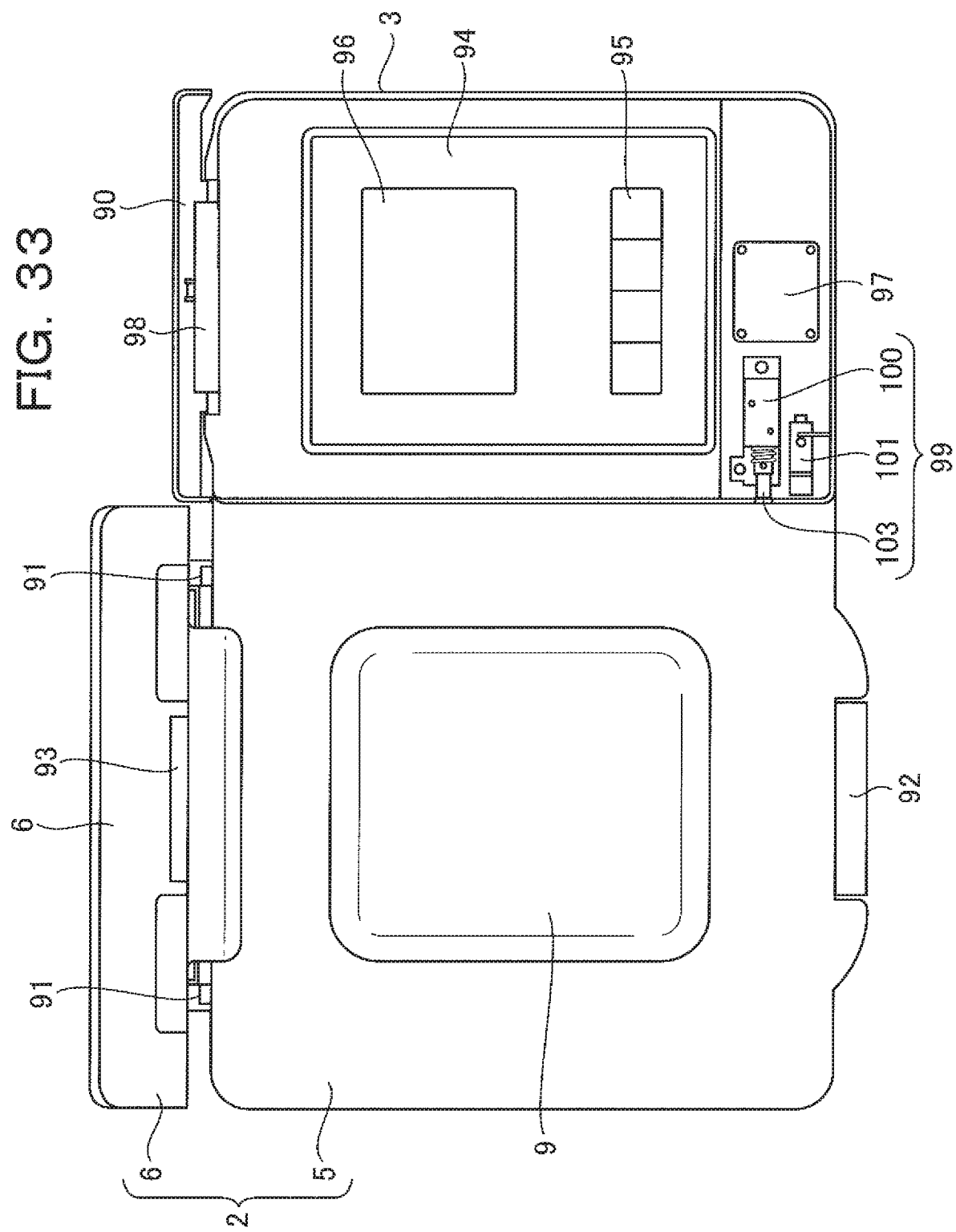
FIG. 33 is an enlarged plan view of the transport box with both the insulating cover body and protective plate open.

FIG. 31 is a diagrammatic perspective view of a transport box according to a twelfth embodiment of the present invention with both the insulating cover body 6 and a protective plate 90 closed, FIG. 32 is a diagrammatic perspective view with both the insulating cover body 6 and the protective plate 90 open and FIG. 33 is an enlarged plan view with both the insulating cover body 6 and the protective plate 90 open.

In FIGS. 31 to 33, the nearer side is the front side of the transport box, or a standing position side where the operator stands in order to take in or out the blood product 23.

As shown in FIG. 32, a hinge part 91 is provided on the back side of the insulating container 5 and the base end of the insulating cover body 6 is supported on the insulating container 5 by the hinge part 91 in a manner to turn between the front side and back side of the transport box as indicated by an arrow in FIG. 31.

A latch body 92 is provided on the front upper lateral surface of the insulating container 5 and a lock part 93 to which the latch body 92 is locked is provided on the front lateral surface of the insulating cover body 6.

As shown in FIG. 33, a recording/display unit 94 is provided over the housing 3 and various operations switches 95 as thin-film switches, a liquid crystal display panel 96 and an information reading section 97 as a thin-film antenna are arranged on its upper surface.

In this embodiment, as shown in FIG. 33, the information reading section 97, which is used relatively frequently to take in and out the blood product 23, is disposed on the most frontward side of the transport box (operator standing position side) and the various operations switches 95, which are used with the second highest frequency, are disposed behind the information reading section 97, and the liquid crystal display panel 96, at which the operator merely takes a look, is disposed behind the operation switches 95.

As shown in FIG. 32, a hinge part 98 is provided on the back side of the housing 3 and the base end of the protective plate 90 is supported on the housing 3 by the hinge part 98 in a manner to turn between the front side and back side of the transport box as indicated by an arrow in FIG. 31.

The protective plate 90 is a transparent synthetic resin plate which is used to prevent the operation switches 95 from being pressed by mistake and protect the operation switches 95 and the liquid crystal display panel 96.

Therefore, during transportation of the transport box, the protective plate 90 is turned down and covers the operation switches 95 and the liquid crystal display panel 96 as shown in FIG. 31. For the sake of operability, the information reading section 97 is shaped and sized so as not to be covered by the protective plate 90.

Figure 34:
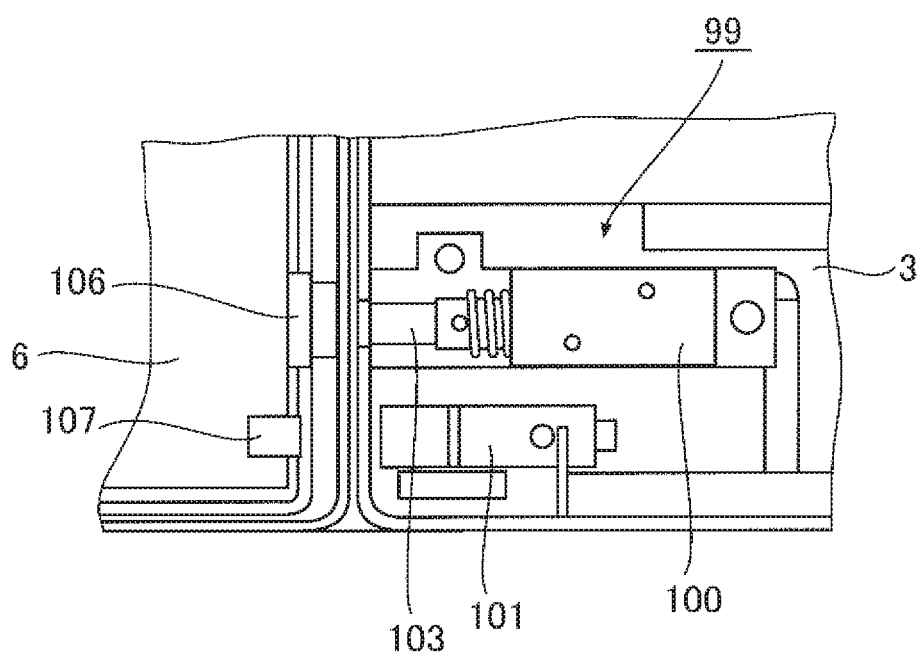
FIG. 34 is a fragmentary plan view illustrating the structure of a security section provided in the transport box.
Figure 35:
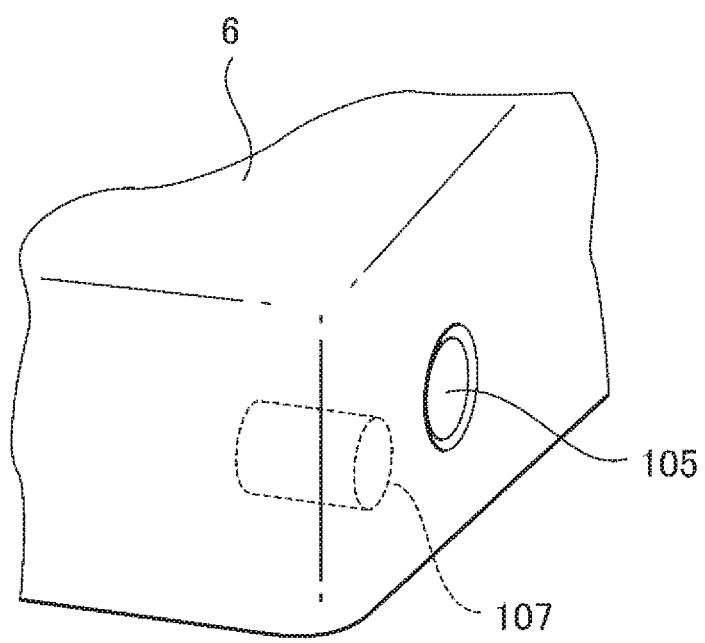
FIG. 35 is a fragmentary diagrammatic perspective view illustrating the structure of the security section provided in the transport box.

FIGS. 34 and 35 illustrate the structure of a security section 99 provided in the transport box. The security section 99 lies from the housing 3's front portion adjacent to the insulating cover body 6 to the insulating cover body 6's front portion adjacent to the housing 3.

Specifically, an electromagnetic solenoid 100 and a magnetic sensor 101 are arranged almost in parallel toward the lateral surface of the insulating cover body 6 at the housing 3's front portion adjacent to the insulating cover body 6. The electromagnetic solenoid 100 and magnetic sensor 101 are covered by a cover member 102 so that they are invisible from outside as shown in FIG. 32.

A notch 104 through which the tip of a lock shaft 103 of the electromagnetic solenoid 100 is taken in and out is formed in a lateral surface of the housing 3 (see FIG. 32).

On the other hand, a shaft receiving member 106 with a cap-shaped cross section which has an opening 105 (see FIG. 35) for insertion of the tip of the lock shaft 103 of the electromagnetic solenoid 100 with the insulating cover body 6 closed is mounted opposite to the electromagnetic solenoid 100 at the insulating cover body 6's front portion adjacent to the housing 3.

The permanent magnet 107 (see FIG. 34) is mounted opposite to the magnetic sensor 101 with the insulating cover body 6 closed.

When the insulating cover body 6 in the state shown in FIG. 32 is turned down frontward and closes the opening part 4 of the insulating container 5, the permanent magnet 107 comes closer to the magnetic sensor 101 and the magnetic sensor 101 detects closing of the insulating cover body 6. According to this detection signal, the lock shaft 103 of the electromagnetic solenoid 100 is automatically protruded and its tip is inserted into the shaft receiving member 106 to lock the insulating cover body 6 automatically so that it is not carelessly opened.

If an attempt is made to open the insulating cover body 6 in this state forcedly, the electromagnetic solenoid 100 and the shaft receiving member 106 might be broken. For this reason, apart from the first lock means including the electromagnetic solenoid 100 to the shaft receiving member 106, this embodiment also includes second lock means including the latch body 92 to the lock part 93. The embodiment is structured so that after the insulating cover body 6 is closed, the key-shaped latch body 92 can be moved and locked onto the lock part 93 for double locking.

FIG. 36 is a plan view of the blood product 23 in which the blood product 23 is hermetically sealed by a double bag 78 and an RFID tag 79 storing individual information on the blood product 23 is attached to the surface of the outer bag 78. Each operator carries an IC card (not shown) which stores ID information on the operator.

When taking in or out the blood product 23 from the transport box, the operator brings the IC card close to the information reading section 97 and the recording/display unit 94 decides whether the ID information stored in the IC card is ID information previously registered in the recording/display unit 94.

If the ID information does not coincide, a warning to the effect that the ID information does not coincide is outputted from the liquid crystal display panel 96 of the recording/display unit 94 and (or) the alarm section (not shown). The electromagnetic solenoid 100 of the security section 99 remains locked.

If the ID information coincides, according to an ID information coincidence signal, the lock shaft 103 of the electromagnetic solenoid 100 is retracted from the shaft receiving member 106 and the first lock means including the electromagnetic solenoid 100 to shaft receiving member 106 is unlocked. The liquid crystal display panel 96 indicates that the second lock means by the latch body 92 should be unlocked and the insulating cover body 6 should be opened. The alarm section gives an audio warning to unlock the latch body 92 and open the insulating cover body 6.

According to the instruction, the operator unlocks the latch body 92, opens the insulating cover body 6, when going to take in or out the blood product 23, brings the ID tag 79 of the blood product 23 close to the information reading section 97 so that the specific information on the blood product 23 concerned as stored in the ID tag 79 is read and it is recorded in the recording/display unit 94 along with the time when the blood product 23 was taken in or out.

When taking-in or taking-out of the blood product 23 is finished and the insulating cover body 6 is closed, the first lock means including the electromagnetic solenoid 100 to shaft receiving member 106 is automatically locked. After that, the second lock means including the latch body 92 to lock part 93 is also locked by operating the latch body 92.

The recording/display unit 94 records the time of taking in or out the blood product 23, the ID information of the operator who handled the blood product 23, specific information on the blood product 23 taken in or out and so on.

Also, the recording/display unit 94 records detected temperatures and times of sampling from the various temperature sensors described in the above embodiments in chronological order. The various data recorded in the recording/display unit 94 can be displayed on the liquid crystal display panel 96 using the operation switches 95 as necessary.

As shown in FIG. 32, the insulating cover body 6 is attached in a manner to extend from the front side to the back side and the opening part 4 of the insulating container 5 (box body 2) and the operation switches 95 and the information reading section 97 of the housing 3 are arranged on the same plane. Therefore, when taking in or out the blood product 23, the operator can take in or out the blood product 23 without wasted motion.

In this embodiment, the magnetic sensor 101 and permanent magnet 107 are used as cover opening/closing detection means to detect automatically that the insulating cover body 6 closes the opening part 4 of the insulating container 5; however, instead, other types of cover opening/closing detection means such as an optical sensor including a light emitting element and a light receiving element, and a mechanical sensor such as a micro-switch may be used.

The characteristics of the transport box according to the twelfth embodiment are summarized as follows.

The transport box is characterized by including:

a box body including an insulating container with an opening part open upward, a heat conducting container with an opening part open upward being attached to the inside of the insulating container to house an object of transport, an insulating cover body supported on the back side upper end of the insulating container through a hinge part to open and close the opening part of the insulating container, an electronic temperature control unit having a Peltier element thermally connected to the heat conducting container, and a temperature sensor for controlling the temperature in the heat conducting container; and a component housing adjacent to and integrated with the box body, the component housing including:

an information reading section for reading specific information on the object of transport being taken in and out of the box body and ID information on each operator and a recording/display unit for recording and displaying temperature information detected by the temperature sensor; and lock means for automatically locking the insulating cover body to prevent opening of the insulating container, in which the information reading section and lock means are located on the front side of the temperature-regulated transport box as the operator standing position side of the component housing and the recording/display unit is located in a more backward position of the temperature-regulated transport box than the information reading section.

The above embodiments have been described on the assumption that a blood product is transported but the present invention is not limited thereto; the invention may be applied to transportation of other objects which require strict temperature regulation, for example, iPS cells (induced pluripotent stem cells), ES (embryo-stem) cells, STAP (stimulus-triggered acquisition of pluripotency) cells, organs to be transplanted, enzymes, and various bio samples.

In addition, it may also be used as a transport box for tissues or cells for regenerative medicine. Recently, research for transportation nearly at the body temperature has been conducted in order to prevent deterioration in cell activity instead of conventional cold transportation. For such application purposes, a transport box which is compact and lightweight and provides a wide set temperature range and uses a Peltier element capable of accurate temperature regulation is suitable. When a transport box is used for regenerative medicine, not only control to maintain a prescribed temperature but also other functions, such as an internal gas component adjustment function, a pressure function and a vibration absorption function, are required.

REFERENCE SIGNS LIST

1 . . . Transport box,
5 . . . Insulating container,
6 . . . Insulating cover body,
7 . . . Opening part,
8 . . . Internal heat conducting container,
9 . . . Internal space,
10 . . . Electronic cooling unit,
17 . . . Opening end, 18 . . . Heat absorption side thermal conductor,
19 . . . Heat radiation side thermal conductor,
20 . . . Peltier element,
23 . . . Blood product,
25 . . . Power supply control board,
29 . . . Power supply control temperature sensor,
30 . . . Ambient temperature sensor,
31 . . . Polarity inversion control section,
35 . . . Cover internal side heat conducting plate,
62 . . . Central control section,
63 . . . Peltier element voltage control section,
64 . . . Fan output control section,
67 . . . External heat exchanger temperature sensor,
68 . . . Internal battery temperature sensor,
70 . . . Charging circuit,
71 . . . Charge stopping means

The invention claimed is:

1. A temperature-regulated transport box comprising:
an insulating container having an opening part on one side;
an internal heat conducting container mounted inside the insulating container to house an object of transport;
an insulating cover body to open and close the opening part of the insulating container; and
a temperature control system to keep a temperature of an internal space formed by closing the opening part of the insulating container by the insulating cover body, at a prescribed temperature, wherein an inwardly protruding portion protruding toward an opening end of the internal heat conducting container is provided on an inner surface of the insulating cover body and a cover internal side heat conducting layer is provided on an internal side inner surface of the inwardly protruding portion,
when the opening part of the insulating container is closed by the insulating cover body, the cover internal side heat conducting layer provided in the inwardly protruding portion is located inward near the opening end of the internal heat conducting container,
the temperature control system includes:
an electronic cooling unit having a heat absorption side thermal conductor, a heat radiation side thermal conductor, and a Peltier element interposed between the heat absorption side thermal conductor and the heat radiation side thermal conductor, the electronic cooling unit being attached to a first sidewall of the internal heat conducting container; an internal temperature display temperature sensor mounted on the outer lateral surface of a second sidewall of the internal heat conducting container at a portion where a temperature close to an internal center temperature of the internal heat conducting container is indicated, the first sidewall and the second sidewall being disposed opposite to each other, wherein
power supply to the Peltier element is corrected according to a result of detection by the internal temperature display temperature sensor, and
a heat pipe is attached to the internal heat conducting container and surrounds an outer circumferential surface of four sidewalls of the internal heat conducting container, the four sidewalls extending in a same direction from a periphery of the bottom of the internal heat conducting container, the four sidewalls including the first sidewall and the second sidewall;
a power source to supply power to the Peltier element;
a power supply control temperature sensor mounted on an outer lateral surface of the internal heat conducting container near a portion in contact with the heat absorption side thermal conductor or on the heat absorption side thermal conductor;
an ambient temperature sensor to detect an ambient temperature around the temperature-regulated transport box; and
a power supply control board to control an amount of power supplied to the Peltier element according to a detection signal from the power supply control temperature sensor, and
the power supply control board receives the detection signal from the ambient temperature sensor and adjusts a value of current supplied to the Peltier element according to the ambient temperature so as to stabilize the temperature of the internal space at a set temperature.

2. The temperature-regulated transport box according to claim 1, wherein the object of transport is a blood product or tissues or cells for regenerative medicine.

3. The temperature-regulated transport box according to claim 1 wherein an upper end of the internal heat conducting container is expanded outward at a curved portion and the upper end is disposed inside the insulating container.

4. The temperature-regulated transport box according to claim 1,
the temperature control system further comprising an external heat exchanger temperature sensor mounted on the heat radiation side thermal conductor, wherein
when the ambient temperature around the temperature-regulated transport box rapidly changes, in addition to correction of power supply to the Peltier element by the ambient temperature sensor, a condition to supply power to the Peltier element is temporarily changed according to a result of detection by the external heat exchanger temperature sensor.

5. The temperature-regulated transport box according to claim 4, wherein the heat pipe has a plate-like shape.

6. The temperature-regulated transport box according to claim 1,
the power supply control section comprising: an external power source input section to receive power from an external power source; and an internal battery input section to receive power from an internal battery built in the temperature-regulated transport box, wherein
while power is supplied to the Peltier element by the external power source, the internal battery is charged, an internal battery temperature sensor is provided to detect a temperature in a vicinity of the internal battery or a temperature of the internal battery, and a charge stopper is provided to stop charging of the internal battery when the temperature detected by the internal battery temperature sensor becomes close to 0° C. or 40° C. or more.

7. The temperature-regulated transport box according to claim 6, wherein the heat pipe has a plate-like shape.

8. The temperature-regulated transport box according to claim 1, wherein the heat pipe has a plate-like shape.

9. The temperature-regulated transport box according to claim 8, wherein the object of transport is a blood product or tissues or cells for regenerative medicine.

10. The temperature-regulated transport box according to claim 1,
the power supply control section comprising a polarity inversion control section to invert polarity of voltage supplied to the Peltier element, wherein
when the ambient temperature is lower than the temperature of the internal space and the temperature of the internal space decreases, the polarity of the voltage supplied to the Peltier element is inverted by the polarity inversion control section to keep the temperature of the internal space constant by heating.

11. The temperature-regulated transport box according to claim 10, wherein the heat pipe has a plate-like shape.

12. The temperature-regulated transport box according to claim 10,
the power supply control section further comprising: a fan to send air to the heat radiation side thermal conductor; and
a fan output control section to control output to the fan, wherein while the temperature of the internal space is kept constant by heating, driving is done without stopping the fan by the fan output control section.

13. The temperature-regulated transport box according to claim 12, wherein the heat pipe has a plate-like shape.

* * * * *